(12) United States Patent
Elgebaly et al.

(10) Patent No.: US 10,895,572 B2
(45) Date of Patent: *Jan. 19, 2021

(54) AUTOPHAGY-RELATED NOURIN GENE-BASED RNA NETWORK AS EARLY BIOMARKERS FOR CARDIAC PATIENTS

(71) Applicant: Nour Heart, Inc., Vienna, VA (US)

(72) Inventors: Salwa Ahmed Elgebaly, Vienna, VA (US); Marwa Matboli Sayed, Vienna, VA (US)

(73) Assignee: NOUR HEART, INC., Vienna, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/252,402

(22) Filed: Jan. 18, 2019

(65) Prior Publication Data
US 2019/0383809 A1 Dec. 19, 2019

Related U.S. Application Data

(60) Provisional application No. 62/686,184, filed on Jun. 18, 2018.

(51) Int. Cl.
| | |
|---|---|
| A61K 48/00 | (2006.01) |
| C07H 21/04 | (2006.01) |
| G01N 33/566 | (2006.01) |
| C07K 16/24 | (2006.01) |
| G01N 33/563 | (2006.01) |
| G16H 50/50 | (2018.01) |
| G16H 10/40 | (2018.01) |
| G16H 10/60 | (2018.01) |
| G16H 50/30 | (2018.01) |
| G16H 50/70 | (2018.01) |
| G16H 50/20 | (2018.01) |
| G16H 20/10 | (2018.01) |
| G16B 20/20 | (2019.01) |
| C12Q 1/686 | (2018.01) |
| C12Q 1/6883 | (2018.01) |

(52) U.S. Cl.
CPC .......... *G01N 33/566* (2013.01); *C07K 16/24* (2013.01); *C12Q 1/686* (2013.01); *C12Q 1/6883* (2013.01); *G01N 33/563* (2013.01); *G16B 20/20* (2019.02); *G16H 10/40* (2018.01); *G16H 10/60* (2018.01); *G16H 20/10* (2018.01); *G16H 50/20* (2018.01); *G16H 50/30* (2018.01); *G16H 50/50* (2018.01); *G16H 50/70* (2018.01); *C12Q 2600/112* (2013.01); *C12Q 2600/158* (2013.01); *C12Q 2600/178* (2013.01); *G01N 2800/325* (2013.01); *G01N 2800/50* (2013.01); *G01N 2800/56* (2013.01)

(58) Field of Classification Search
CPC ............... A61K 31/713; C12N 15/113; C12N 2310/141
See application file for complete search history.

(56) References Cited

U.S. PATENT DOCUMENTS

| | | | |
|---|---|---|---|
| 5,403,914 | A | 4/1995 | Elgebaly |
| 5,606,027 | A | 2/1997 | Elgebaly |
| 7,659,091 | B2 | 2/2010 | Elgebaly |
| 7,662,571 | B2 | 2/2010 | Elgebaly |
| 2006/0063199 | A1 | 3/2006 | Elgebaly |
| 2010/0119594 | A1 | 5/2010 | Elgebaly |

OTHER PUBLICATIONS

Tijsen, AJ, Pinton, YM and Creemers, EE. Circulating microRNAs as diagnostic biomarkers for cardiovascular diseases. Am J Physiology Heart Circ Physiol 303: H1085-H1095, 2012. Review.

Paiva, S and Agbulut, O. MiRroring the Multiple Potentials of MicroRNAs in Acute Myocardial Infarction. Frontiers in Cardiovascular Medicine, 4(73), 1-18, 2017. Review.

Wang, C and Jing, Q. Non-coding RNAs as biomarkers for acute myocardial infarction. Acta Pharmacologia Sinica 39: 1-9, 2018. Review.

Sluijter JPG, et al. Extracellular vesicles in diagnosis and therapy of the ischemic heart: Position Paper from the Working Group on Cellular Biology of the Heart of the European Society of Cardiology. Cardiovascular Research. 114, 19-34, 2018. Review.

Du, Z. et. al. Integrative analyses reveal a long noncoding RNA-mediated sponge regulatory network in prostate cancer. Nat. Commun. 7:10982 DOI:10.1038/ncomms10982 (2016).

Adams, J. Markers to define ischemia: Are they ready for prime time use in patients with acute coronary syndromes? Current Cardiology Reports, 6(4):253-8, 2004. Review.

*Primary Examiner* — Amy H Bowman

(57) ABSTRACT

The present invention provides a molecular network, devices, and assays for early diagnosis of ischemic cardiac events in patients experiencing chest pain. The invention allows for the differentiation of chest pain due to ischemic cardiac events and other non-cardiac causes. The invention provides a Nourin-based RNA molecular network composed of lncRNA-CTB89H12.4, hsa-miRNA-137, and FTLH-17 mRNA as an autophagy-related RNA panel linked to each other and to cardiovascular ischemia to specifically diagnose ischemic cardiac events. The invention further demonstrates that the down-regulation of RNA-CTB89H12.4 after an AMI event, resulted in the up-regulation of hsa-miRNA-137 and activation of FTLH-17 mRNA with an increased translation and production of Nourin protein; a cardiac-derived biomarker. These Nourin multiple genes can, therefore, be used alone, and in combination with the protein-based Nourin measured by antibodies comprising of the epitope sequence f-MII to increase the early diagnosis of ischemic cardiac patients with a high degree of accuracy.

4 Claims, 22 Drawing Sheets

Specification includes a Sequence Listing.

ferritin heavy polypeptide-like 17 [HOMO Sapiens]
SequenceID: NP_114100.1  Length: 183  Number of Matches:1

Range 1: 19 to 24  Genpept  Graphics                    ▽ Next Match  △ Previous Match

| Score | Expect | Identities | Positives | Gaps |
|---|---|---|---|---|
| 21.4 bits(43) | 62 | 6/6(100%) | 6/6(100%) | 0/6(0%) |

Query  9   AAINSH  14
           AAINSH
Sbjct  19  AAINSH  24

FIG. 2

| | Ensembl Gene Id | miRNA name | miTG score | Also Predicted | |
|---|---|---|---|---|---|
| 1 | ENSG00000132445 (FTHL17) | hsa-miR-548ar-3p | 0.977695570507030 | ☐ ▨ | > |
| 2 | ENSG00000132445 (FTHL17) | hsa-miR-589-5p | 0.977113273205747 | ☐ ▨ | > |
| 3 | ENSG00000132445 (FTHL17) | hsa-miR-548e-3p | 0.958778553040087 | ☐ ▨ | > |
| 4 | ENSG00000132445 (FTHL17) | hsa-miR-4766-5p | 0.953774408116615 | ☐ ▨ | > |
| 5 | ENSG00000132445 (FTHL17) | hsa-miR-137 | 0.916733991921927 | ☐ ▨ | > |
| 6 | ENSG00000132445 (FTHL17) | hsa-miR-548a-3p | 0.858381214044193 | ☐ ▨ | > |
| 7 | ENSG00000132445 (FTHL17) | hsa-miR-548az-3p | 0.845149519537140 | ☐ ▨ | > |
| 8 | ENSG00000132445 (FTHL17) | hsa-miR-548f-3p | 0.837928897852551 | ☐ ▨ | > |
| 9 | ENSG00000132445 (FTHL17) | hsa-miR-4639-5p | 0.816317602779086 | ☐ ▨ | > |

FIG. 6

| name | mirAccession | geneName | targetSites | bioComplex | clipReadNum | CancerNum |
|---|---|---|---|---|---|---|
| hsa-miR-137 | MIMAT0000429 | RP11-206L10.11 | 1 | 1 | 6 | NoData |
| hsa-miR-137 | MIMAT0000429 | RP11-3782.1 | 1 | 1 | 99 | NoData |
| hsa-miR-137 | MIMAT0000429 | RP11-14886.1 | 1 | 1 | 9 | NoData |
| hsa-miR-137 | MIMAT0000429 | OIP5-AS1 | 3 | 13 | 836 | NoData |
| hsa-miR-137 | MIMAT0000429 | AF127936.7 | 1 | 1 | 12 | NoData |
| hsa-miR-137 | MIMAT0000429 | CTB-89H12.4 | 1 | 2 | 1378 | NoData |

FIG. 7

```
caaatgccat tgaaaccgct agtcttattt cctttctact tttctttggc actcttactg    60
cctgtaagga gtagaactgt tagggcacac tgttgctata cagtttaact cccattttca   120
tgttttgtct ttcttttccc atttctgggg cttacctcct gatacctgct tactttctgg   180
aagtagtggg caagtaagat ttggctcttg gtttctaatt tttaaatttc tgaatactgc   240
cctagtctga acttggcctt tatagattaa tctttgcttc acattttag tgttgtattt    300 aaactatttt ataatttaaa aatagattct aatctgaaga tacttttcaa gaaatattat   360
taactgatgt catcctcatc ccagcagctc atctgttagg aatgaagttg agatgcttct   420
attccatgtt tttgtatttg ggaaggattc aaagttgaag gtttattgtc gttgggtttt   480
tcagatggtg acatgtaaac tcaggatagc aaaccctaat gttcacacag tgctctgcct   540
ctgcatctca gttgggatag ttgctccttt tgagtgtttt aatcatcgta taactaatca   600
tagtgccaag aagttcataa tgtgttatgt agctaatgtc actgaaaaac agtcctacca   660
ttttaggtaa gaccaaacag agtctctaac ccaaggactt gttacacctg acaacctata   720
gtatatttgc tttttctcac aaaatgaaac caattttgcc gaaagctagc tgggataata   780
ggatcatcac aagttgcagt ttctataact aaaattagat tgaaatctct tctgacctag   840
aacattttac ttcaggcatt cagcagattt cagaaagaat taccttattt taagttagtt   900
tctttgttag tttactgtgt gtctcttatt caataaacaa gcagaatttg tgtcctgccc   960
```

FIG. 15A

```
tatccatgtc ttaaagatga gaagttggat ccactgagtt agtttcattg gggcggggga    1020
aagaactgta attaaacttg tttaatcctt attttgtatt gtagctattt tttgtaaaag    1080
caacttaaaa tcttttaaaa attttatagt gacattagag acaatggtca tacaaattat    1140
cacataaaca tggacttgaa aaattaggct tttcataaaa cacatcacat gtcattgact    1200 gcttttaga  aatacacttc caaggcagta catctgtatt gctactgaaa agtgccattt    1260
cacagaacac agacttcttt ttgctctttg acatcttgaa acatctgtt  tttctttttt    1320 aatacaaaac tttgtgctca agacaaatct tacatgaaac tctcataaac catgaaaatg    1380
tagctggcct tcgggcctta ggcatgaaat aagcatgagg aacatattcc cctaacttct    1440 accccagcc  cagcaagtta tcctttaaga aatctcctag gaattctgga gtttgaaaac    1500
aattgctcta tgttattcct gcttccagtc tctaagtaac aagggcattt aaaagcatag    1560
tctcttaagg tccactatag tggttcttta tttaaggaat aactcagctg ggtgcagtgg    1620
ctcacgcctg ttatcccagc actttgagag gctgaggcaa gcagatcact tgaggccagg    1680
agttcgagag tctggccaac atggtggaaa cccatctcta caaaaaatac aaaaattagc    1740
caggtgtggt ggcgtgcacc tatggtccca gctatttggg aggctgaggc aggagaattg    1800
cttgaacctg ggaggtggag gttgcagtga gccaagattg tgccgctgca ctccagcctg    1860
ggtgacagag tgagactctg tctcaaaaaa aaaaaaaaa  ggaactcata cagctcaatg    1920
```

FIG. 15B

```
attcattgat cccaataata aatcgtttta ataatgatga aacatccta ctggggtttt      1980 cttgttaaaa actttaggac aggcgcagtg gctcatgcct gttattccaa cacatttggg      2040
aggctgaggt gggagaattg cttgaccccta ggagttctag acttgcctgg gccacatagt    2100
aagaccctgt cccagctccc tccaacatcg tccccaaccc ccccccccc aaaaaaaaaa      2160 agcgccaggc gcagtagtga gtgcctgtga tcccagctgt gttgggaggc tgaggtggga     2220
gtatcacctg agccctggag gttgaggctg caatgagagc tgtgatcatg ccactgcact     2280
ccagcctggg caacagatga gaccctgtgt cacaacaagg aattttttaga aggtgctttt    2340 tatattactc ttcacagagt taaattttca gaggatttag tattattgaa ctaagtttca    2400
taagtgtatt ttaagcaagt aaatctctaa tgtaggaaaa tccccaaaat ggtagcattt    2460
actaatgttt tatatggtaa tttttgaaaa atatatctga tatttcttca gtaaaaatgg     2520
tgttgtttta ataacttaat aagaatgttt aaagattctt taagtctggc ttatctagct    2580
aatgtgggcc tattaaataa taggcagact tctgccttcc ttatattctt tagatctttt    2640
caaatactcc attccaatat ccatcaaaag acttctcttt atgccactta ttatctatac    2700
tagtttttaa tgttcaatta ctacaagatt ataattactg tttttattca tgttcccaag   2760
aaaaatacat aagattcaca cccaacacac ttcgaaattt atttcactcc ctttgactat    2820
atgtgattat caaaaaagta ttttttcaaga tattaaaaat aagtaaagga aatgaaata    2880
```

FIG. 15C

```
tttttaggac attcaaaatc taatgaagtt cagtgtttct ttaattgagg gcaggcagag      2940 gtggggaga  atttcagaag gtagtgaacc caaaggtgga ttcttggata attctactat      3000
tctgtactct catcatctta acccatctgt ttactaccct aaccatagtt actaagcaga      3060
gttttatcat aataatatag acagctctca aagtattgac attcagaggg gattacaaat      3120 attattttc  tatcatattg acctaccatg tccacagtct tccttgaatt accttccagt      3180
tttactgggc tgcatctacc gtttatgtct agtttgactt tttctgagtt caccaattgc      3240
tgctaggaat gtgctggtca ctcagcagca cacccacatc acaggggaag attttgaaat      3300
acctggacag tctgaacaca ctgctctgaa tacactcaat tctaagaagt accagggaac      3360
cgcatcttct tgctgaaatc ttgaatttttt gtcagctttt tttttactg tggacagtaa      3420 agctggaaag atctaaataa cccaacagga aatgcggatg aaagtgcaag agttggtttg      3480
tggtcatctg gagtccatgt ctccaagact gctggacctt caaattctgc aacttgttag      3540
atcatctgga tgatagcaca actgttagaa gacctagaag aatacagcgt tgctatgact      3600
cagtggtgtt gaatgcagac catctaccag ctggggaaag aatcaattat aaacaggaat      3660
aaagggattc attcctcatt ttaactgatg ttacagtgaa gatgggttct tgaactcttg      3720
gaagcctgga tgagccacct aatctgcaag ataaaaacca aagaccaatg cgtattgggg      3780
aaaagaatgc ttagtactgc aagactgttg aatacctgtt gaatattcct attgaggttt      3840
```

FIG. 15D

```
tttcctaaac atacttcagt aacatcttag gacaattcac tggagaaatg ttgatccctg      3900
gctggaatgt cataccattg acccatttga agagttaaag ctggatttga ctgctctatt      3960
ctaccaggaa tattgttagg gtagccttt  accagtttct aaacaattgt aatcatttat      4020
tgactcagca attcctcaga taacaggtca aagatgtac  agatacattc tgaagttttc      4080
ttgctattaa aggcacaaga gtttccttgt attttgactg acaatgtagc atgtttccat      4140
tttagtttgt tagtgatggt ggttttccct tgaaagcca  tttggtatat tcaccataac      4200
aattagttta atatgattac ataagaaaac tatgataaaa cccagcaatt ttagtagttg      4260
tgaaaatacg tttttaaat  catgtttaag aagaattgca agacttgaaa ccaaatcctg      4320 atggggaat  tctgtttaat cctgtttaat ctgtttaatt tctgtttaat ccttagtttc      4380
ttaacctgca tagcttatcc tgtattgtac ttttttctt  ttttaaactc caaacaaga       4440 agcttgaaac ttttcctgta ttttaaaatt gaaatttggt cacagggtat agtcagattt      4500
ttattaaggt ttggtttgac aacctttaaa agaaaggttt acctcgctaa tacttcttaa      4560
taacatgcat caaatgatat tccctatggt gaagtatatt ctcaaagtta tgttatcttt      4620 cattttggc  atttggtgct tatggactta gtacccaggc aacaaagatc tattatgcac      4680
ctactctctt gtatgttcgc tattatttcc caaaaaaaa  aagggcata  tatgcataag      4740 aaataaatat tagaattatt ttgtttctcc cacaaagccc atgggagatg gcccaacaaa      4800
```

FIG. 15E

```
tgtttaaaaa gtaaagaaag ctgggcacgg tggctcccac ctgtaacccc cacactttgg        4860
gaggccatgg cgggtggatc acgaggtcag gagtttgaga ccagcctggc caacacagtg        4920
aaactgtgtc tctactataa atacaaaaat tagccaggca tggtggcagg cacctatagt        4980
cccagctact caggaggctg aggcaggaga tcgcttgaa  cccaggaggc agaggttgcg        5040
gtgagccaag atcatgccac tgccctccag cctgggtgac agagcgagac tgtctccaaa        5100 aaaaagaaa  aagaactaa  agaaaagga  gcagtttatg attgaagaaa acatgacctg        5160
ggctgaagaa gtgaggattg attggagtgg gctagaatga gctatagttt ctagctcatt        5220
tgtaaggagg tagacaaagg agcattggtg cctcagagtg ggtgtctggt gagaggaaaa        5280
acggtgctta agagattttc aggctattgc tgtgggacag gcatattttc tcccttgcc         5340 tttagctgta gataaagtgt ggttatgacc tgaggcttct tgtattcaaa cttggcctag        5400
ggcctatgta gaggccctag ggtctacttg tggtggagga gggaagtatt tgtagaatgt        5460
gtaggcttga gaagtaaata aagccaaaaa agcatcactt gcttacattt ttaaatgagt        5520
cacaaaacaa tctttctaat gcggccggta agaagttttt aaaggtctaa ggtttctcta        5580
cagaaattac atgcttctca ggtctttgtt tagtaaaata atacagataa ttatgctttg        5640
aatgcattta ttattaaagc taaccgtttt aatttgtgtc agaaataatt tgtgcctatg        5700
gtaggattaa aattgtattc tttagttaaa gcaaagcaat ctgttttca  ttgatttgat        5760
```

FIG. 15F

```
aaatatgtga atgcctaata tgttctgcat atgtaaaaat gcagaaacat gctcatttga    5820
attactaata attattttag tatgctgaga ggctttgaat tcactgtacc actccttcct    5880
agagtcattc aaaacagaaa aaattagttt taagtataga ttcatgtttt tctgttttaa    5940
aaagttgagc taatactttt cacaagagac gaaataacat gagccactat aattattggc    6000
tcagttccac ccaatttcca tattttgggt gtaatttaaa attttgact tggaatttta    6060 actttttttt tgttttgatt ttttaccagg tttctaagca tgaattgagg aacagaagaa    6120
gcagagcaga tgatcggagc agcatttgtt tctccccaaa tctagaaatt ttagttcata    6180
tgtacactag ccagtggttg tggacaacca tttacttggt gtaaagaact taatttcagt    6240
ataaactgac tctgggcagc attggtgatg ctgtatcctg agttgtagcc tctgtaattg    6300
tgaatattaa ctgagatagt gaaacatggt gtccggtttt ctattgcatt ttttcaagtg    6360
gaaaagttaa ctaaatggtt gacacacaaa aattggtgga gaaattgtgc atatgccaat    6420 ttttgttaa aacctttgt tttgaactat actgctttga gatctcattt cagaagaacg    6480
gcatgaacag tcttcagcca cagttgtgat ggttgttaaa tgctcacaat tgtgcattct    6540
tagggttttt ccatccctgg ggtttgcaag ttgttcactt aaaacattct taaaatggtt    6600
ggcttcttgt ctgcaagcca gctgatatgg tagcaaccaa agattccagt gtttgagcat    6660
atgaaagact ctgcctgctt aattgtgcta gaaataacag catctaaagt gaagacttaa    6720
```

FIG. 15G

```
gaaaaactta gtgactacta gattatcctt aggactctgc attaactcta taatgttctt         6780
ggtattaaaa aaaaagcata tttgtcacag aaatttagtt aacatcttac aactgaacat         6840
gtatgtatgt tgcttagata aatgtaatca ctgtaaacat ctatatgatc tgggattttg         6900
tttttatttt gaaatgggag cttttttgtt tacaagttca ttaaaaacta aaaactgttt         6960
ctgtaaggaa atgagatttt tttaaacaa caaaaaatgc cttgctgact cactattaaa         7020
taaaaatctc cccaattttt tgatagacta cttcaagcca tttgttacat ggtattcctt         7080
tgcaagtcaa tttaggtttc gtgttataac ttttcctctt tttttaagaa aaatgaaaaa         7140
agtaattctt ttgtctgaag gggaaaggca ttctttcatt tttttctttt tttttttttt         7200
tttttatgac ttgcaggcac aatatctagt actgcaactg ccagaacttg gtattgtagc         7260
tgctgcccgc tgactagcag ctggactgat tttgaataaa aatgaaagca ttaaagggtt         7320
tccctacaaa acattttct ttaaaatact tttgaaatgg ctataagcag ttgactttca         7380
cccttggaga gcatcacact gtgtgaggtt cagtgattgt tgaccctccc cagcccctcc         7440
tgcttcttta agttatctgt gtgcgtgcgc ttcctctcaa tcttctttgc acgctcattt         7500 cttttctct gacccatgag aaaggaaaac ttactgatga taatttttaa atagtgtaat         7560
ttattcattt atagcatgtc aggataaatt aaaagaacat ttgtctggaa atgctgccgg         7620
gagcctattg tgtaaatgta ggtattttgt aaaataacct tgaaattgta aattgacacg         7680
```

FIG. 15H

```
tgtttggtca gattgtgtca agtttaattt gttttgtttt cttttttctt ttttttattt    7740
gaaaactact ttagcaataa ttaattccat gattatcaca ttctgccatt aagggatatt    7800
agtaccgtaa tactgaagaa attttattaa gtctgaactt ctggggtagg cagcttcttt    7860
gtttcttttc tatccaccct tgtcggttga ggtatttgtt cttgactaa taaaccettt     7920 gatacttta gccagaaatc agtctcataa agctattttt gagtatagtt tgtgtaaaat     7980
aaaaatgttt agctttggta ataacttcca agctgaactc cctctagcaa gatatttttc    8040
agtgctttta tttactatgc acttagacta tgcactttt ctgaaatatt tttgtaacac     8100
ttttttgtat ttttgccatt tgaaaaggtt gtggtgtagt tggtctgtaa ttaagttgca    8160
gatttaaaac tgctgttagc tttgtaaatc aaaatatagg tgttttttgt cctggtatat    8220
cgtcattcca tctgcagctg gagctggaat cccattgatc ttctagctac cattcattt     8280 cttcactgtt cacaaaagaa gagtgtgaaa ttcagtgaat gctgttacta atcctgttac    8340
gagatgaatc tcatttcacc aaaattaaat tatgttttc cgctaaaatg atgatacaag     8400
ttgaagacac atcactctga aattggaaga cctcaccact taaggctcca cagtggctta    8460
ctcagctgaa ctctaggtta ctactcttta ctttgttcac ccattggggg gtgcagtttt    8520
tttaaaatgt tgggagatgg ccattctaac tactgttgaa tgtctctgtt ttgggaaggt    8580
ataacaagaa ataaaaaaga atatatatga agggagagac tggttatctc ctccca        8636
```

FIG. 15I

AUTOPHAGY-RELATED NOURIN GENE-BASED RNA NETWORK AS EARLY BIOMARKERS FOR CARDIAC PATIENTS

CROSS REFERENCE TO RELATED APPLICATIONS

The current application is a non-provisional patent application of U.S. Provisional Patent Application 62/686,184 filed Jun. 18, 2018.

FIELD OF THE INVENTION

The present invention generally relates to the fields of medicine, physiology, biomarkers, diagnostics, and biochemistry. The present invention particularly relates to an autophagy-related RNA-based biomarker panel linked to each other and to cardiovascular ischemia. More particularly, the present invention relates to early diagnosis and differentiation between diseases or disorders using a protein and molecular network for the detection of RNAs released as a result of certain events.

BACKGROUND OF THE INVENTION

Heart disease is the leading cause of death in women and men worldwide according to the World Health Organization and it is predicted to persist as the one of the main causes of illness due to the progressive aging of population. Ischemia of the heart occurs as a result of diminished blood flow to heart tissue. If this reduction is brief (less than 15 minutes), the ischemic injury is reversible, as seen in unstable angina (UA) patients. But if reduced blood flow is persistent for an extended period of time (more than 15 minutes), irreversible necrotic damage (cell death) occurs which leads to acute myocardial infarction (AMI-heart attack). Currently, no blood test can specifically identify unstable angina patients. Tests for heart attacks cannot be done until several hours (three to six hours) after presentation of symptoms in order to allow enough substances to be released in the blood by dead heart tissue.

The root cause of acute coronary syndromes (ACS) is unstable plaque in the coronary artery. These syndromes represent a continuum of ischemic disease ranging from unstable angina (UA) to heart attack (acute myocardial infarction-AMI) and to large areas of heart cell death. Each year in the U.S., between 6 to 10 million individuals present annually to Emergency Departments (ED) with clinical signs and symptoms of ACS including chest pain. Of the 6 to 10 million patients presenting annually to the ED with chest pain, up to 90% do not have a heart cause for their symptoms. In the U.S., the high rate of chest pain admissions of non-heart origin is as high as 60%. Accordingly, there is an urgent need for an early and accurate diagnosis of ACS patients to warrant immediate medical care, which would reduce mortality and improve prognosis. A quick blood test is needed that can accurately rule in or out the 10% of ACS heart patients, who are equally divided (50:50) between UA and heart attack. Currently, there is no biomarker to identify patients with unstable angina seen in the ED with chest pain. The misdiagnosis of unstable angina patients in the ED is the highest source of medical malpractice lawsuits in the U.S.

It is known in the art that AMI is associated with the release of proteins and nucleotides (RNAs) as a result of ischemic damage to cardiac tissue. Nourin is a 3 KDa N-formyl peptide rapidly released within 5 minutes by reversible ischemic myocardial tissue, such as in the case of UA, and by necrotic myocardial tissue, such as in the case of AMI. The formylated peptide Nourin is a potent inflammatory mediator which stimulates leukocyte chemotaxis, adhesion and activation to release a number of cytokine and chemokine mediators, adhesion molecules, digestive enzymes and free radicals. In vivo, the injection of human cardiac Nourin into rabbit skin resulted in an acute inflammatory response within the first 30 minutes characterized by a significant neutrophil infiltration. Nourin can, thus, be characterized as an Alarmin that promotes the innate immune response since it is rapidly released by local myocardial tissues following ischemia and contributes to the initiation and amplification of post-reperfusion myocardial inflammation. As such, Nourin can be an important therapeutic target. Nourin works as a ligand on leukocyte formyl peptide receptors (FPR) that are important potential therapeutic targets to control early and late post-reperfusion inflammation and injury. The cardiac-derived Nourin was purified from cardioplegic solutions collected during cardiac arrest (i.e., reversible ischemia) from patients who underwent cardiopulmonary bypass surgery for coronary revascularization. The amino acid sequence of Nourin released by reversibly ischemic human hearts is formyl substituted-MIINHNLAAINSHRSPGADGNGGEAMPGGGR (SEQ ID NO:15) confirmed by mass spectrometry analysis.

Using both the functional leukocyte chemotaxis assay and the ELISA immunoassay, studies demonstrated that the cardiac-derived Nourin peptide is rapidly released by ischemic heart tissue while it is still "viable" before cells are dead, as well as by necrotic hearts. Consistent results showing the "early" release of Nourin by ischemic hearts were demonstrated using various species (human, dog, rat and cow) as well as several models of ischemic injury to include (1) AMI (necrotic), (2) global cardiac arrest (necrotic), (3) cardiopulmonary bypass surgery (reversible) and (4) heart transplantation (reversible). Unlike Troponin, Nourin was detected in fresh blood samples collected from ACS patients as well as from frozen samples stored at −70° C. for 3 years.

Currently, Troponin released by necrotic heart tissue is the most widely used biomarker for AMI. However, Troponin is a marker of cell death and have certain drawbacks. For example, the Troponin complex is not highly stable as an extracellular protein, and thus its usefulness as a marker for AMI is diminished in samples that have been stored. Troponin also has low specificity where 50% of the time the elevated levels of Troponin give false positives for non-ischemic heart attack patients such as renal failure and non-ischemic heart failure.

Although the Troponin test is currently the "Gold Standard" for determining if a patient has had a heart attack, it is a marker of "cell death" and requires three to six hours of waiting after the onset of chest pain in order for Troponin to appear in enough quantities to be measured in blood samples. At this stage, however, a delay is a missed treatment to save ischemic heart tissues and that a critical delay could lead to permanent cardiac damage and higher incidence of heart failure or death. Although the cardiac Troponin level is dependent on infarct size following reperfusion therapy, the actual Troponin level can be misleading due to the washout phenomenon. Moreover, truly elevated Troponin levels have also been detected in tachyarrhythmias, hypertension, myocarditis and patients with chronic renal failure (CRF). Therefore, a multi-marker approach incorporating both biomarkers and clinical scores may improve the diagnostic accuracy.

Therefore, a need exists in the art for a better test to diagnose unstable angina and myocardial infarction that is "earlier" and more "specific" than Troponin. Since AMI is a leading health care threat to human lives, early and accurate diagnosis warrant immediate medical care, which would reduce mortality and improve prognosis.

Additionally, there is a need for a biomarker of ischemic injury without concomitant cell death that can detect subclinical or silent myocardial ischemia without infarction, as well as low-grade myocardial ischemia without cell death. This biomarker could also be used to monitor cardiac disease progression and predict drug therapy response in clinical trials.

SUMMARY OF THE INVENTION

Generally, in one aspect of the present invention, a novel Nourin gene-based RNA molecular network is disclosed for the early diagnosis of and differentiation between diseases or disorders using molecular network for the detection of RNAs released as a result of certain cardiac events.

In another aspect of the present invention, the novel molecular network has a high stability and is often present in tissue disease's specific expression and can be measured with high sensitivity and specificity.

In yet another aspect of the present invention, the novel Nourin molecular network disclosed therein is composed of lnc-RNACTB89H12.4, hsa-miRNA-137, and FTLH-17 mRNA can be utilized alone, and in combination with the Nourin protein for early diagnosis of acute coronary syndromes (ACS) patients presenting with chest pain to hospital Emergency Departments (ED) and outpatient clinics to allow crucial intervention. Early intervention of ischemic heart patients can abort infarction and save heart muscles. The molecular Nourin RNA network alone and in combination with the Nourin protein can also diagnose AMI patients earlier than Troponin; differentiate cardiac from non-cardiac patients presenting with chest pain to hospital ED and outpatient clinics; monitor disease progression; and predict drug therapy response in clinical trials. The novel Nourin molecular network disclosed therein and Nourin protein have the potential to additionally diagnose subclinical or silent myocardial ischemia without infarction, as well as low-grade myocardial ischemia without cell death; screen CAD patients for risk assessment to predict which patients are at risk for developing AMI; screen heart transplantation patients' blood samples for cardiac allograft inflammation and, thus, reduce heart biopsies; and determine the risk level of heart patients experiencing chest pain who present to hospital ED and outpatient clinics and provide risk stratification of AMI patients.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWING

The accompanying drawings are included to provide a further understanding of the invention, and are incorporated in and constitute a part of the present invention and, together with the description, serve to explain the principle of the invention. Bioinformatic analysis was done using BLAST program to retrieve relevant gene to the Nourin-1 peptide sequence formyl substituted-MIINHNLAAINSHR (SEQ ID NO:16) that is the N-terminus portion of the Nourin peptide sequence and relevant to AMI based on previous microarray studies. In the drawings, FIG. 1 indicates a snapshot of expression of Atlas database showing retrieving target gene involved relevant to the Nourin-1 peptide sequence formyl-MIINHNLAAINSHR. https://blast.ncbi.nlm.nih.gov/Blast.cgi?PROGRAM= blastp&PAGE_TYPE=BlastSearc h&BLAST_SPEC=OGP_ 96-06_ 9558&LINK_LOC=blasttab&LAST_PAGE=blastn&QUERY=FMIINHNLAAINSHR FIG. 2 indicates a print screen showing BLAST alignment of FTLH-17 with Nourin also refer to as Nourin-1 peptide sequence formyl-MIINHNLAAINSHR, available at: https://blast.ncbi.nlm.nih.gov/Blast.cgi?PROGRAM=blastp& PAGE_TYPE=BlastSearc h&BLAST_SPEC=OGP_9606_ 95-58&LINK_LOC=blasttab&LAST_PAGE=blastn&QUERY=FMIINHNLAAINSHR https://blast.ncbi.nlm.nih.gov/Blast.cgi#300244535

FIG. 6 indicates a print screen showing miRNA-137 targeting FTLH17 mRNA and it is available at: http://diana.imis.athenainnovation.gr/DianaTools/index.php?r= microT_CDS/results&k eywords=ENSG00000132446& genes=ENSG00000132446%20&mirnas=&descr=&thr eshold=0.7

FIG. 7 indicates a print screen showing the interaction between miRNA-137 and lncRNA-CTB89H12.4. Available at star base database.

FIG. 13 also indicates that the clinical application of the Nourin-based molecular biomarker panel composed of FTLH-17 mRNA, hsa-miRNA-137 and lncRNA-CTB89H12.4 can be used individually and in combination with the protein-based biomarker Nourin for better and faster diagnosis of AMI patients presenting with chest pain at the ED and outpatient clinics.

FIG. 15A-FIG. 15I indicate the sequence listing of the gene sequences for lncRNA-CTB89H12.4 by PatentIn software.

DETAILED DESCRIPTION OF THE INVENTION

Figure 1:
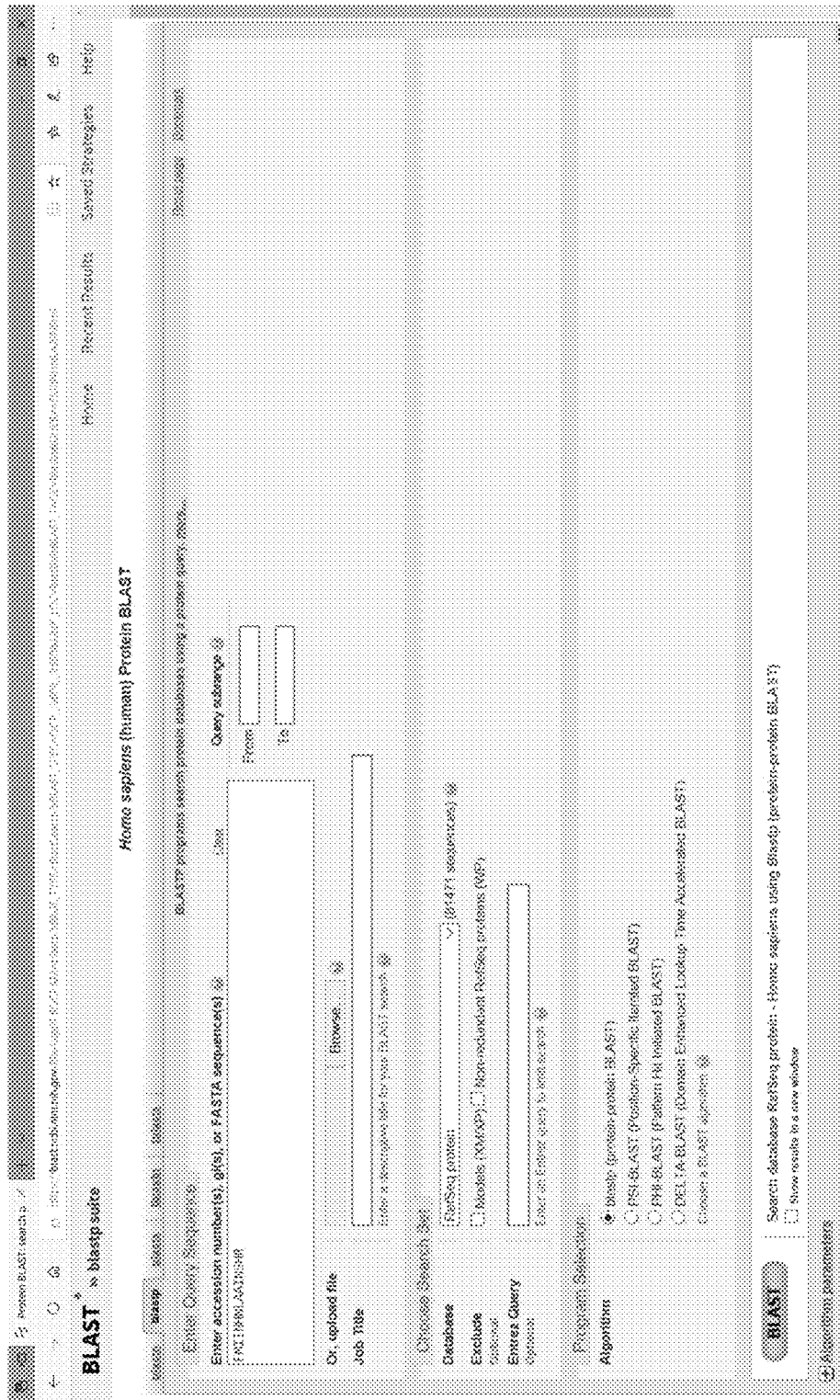

The present invention may be understood more readily by reference to the following detailed description of the invention taken in connection with the accompanying drawing figures, which forms a part of this disclosure. It is to be understood that this invention is not limited to the specific devices, systems, conditions or parameters described and/or shown herein and that the terminology used herein is for the example only and is not intended to be limiting of the claimed invention. Also, as used in the specification including the appended claims, the singular forms 'a', 'an', and 'the' include the plural, and references to a particular numerical value includes at least that particular value unless the content clearly directs otherwise. Ranges may be expressed herein as from 'about' or 'approximately' another particular value. When such a range is expressed it is another embodiment. Also, it will be understood that unless otherwise indicated, dimensions and material characteristics stated herein are by way of example rather than limitation, and are for better understanding of sample embodiment of suitable utility, and variations outside of the stated values may also be within the scope of the invention depending upon the particular application.

Embodiments will now be described in details with reference to the accompanying drawings. To avoid unnecessarily obscuring the present disclosure, well-known features may not be described or substantially the same elements may not be redundantly described, for example. This is for ease of understanding.

The drawings and the following description are provided to enable those skilled in the art to fully understand the present disclosure and are in no way intended to limit the scope of the present disclosure as set forth in the appended claims.

In accordance with one embodiment of the present invention, it discloses a novel AMI-specific Nourin RNA-based integrated competing endogenous molecular network as additional biomarkers for AMI patients. Using the amino acid sequence of Nourin purified from human hearts during reversible ischemia, we identified the Nourin gene-based RNA network through in silico data analysis after BLAST alignment with the Nourin sequence formyl substituted-MIINHNLAAINSHRSPGADGNGGEAMPGGGR (SEQ ID NO:15). We then investigated the serum Nourin gene-based RNA network expression level and pattern in AMI patients and healthy volunteers and compared them to Troponin I level.

Nourin-based RNA Network is an essential part of central dogma, RNA delivers genetic and regulatory information and reflects cellular states. Based on high-through put sequencing technologies, cumulating data show that various RNA molecules are able to serve as biomarkers for the diagnosis and prognosis of various diseases, for instance, cancer and cardiac ischemia. In particular, detectable in various bio-fluids, such as serum, saliva and urine, extra-cellular RNAs (exRNAs) are emerging as non-invasive biomarkers for earlier diagnosis, disease progression, monitor, and prediction of drug therapy response in clinical trials. Although RNAs are unstable in alkaline conditions, they are easy to detect and quantify at very low abundance. Compared to protein biomarkers, RNA biomarkers have more sensitivity and specificity. Standard qPCR technique enables traces of RNA sequences to be amplified and thus captured specifically with high sensitivity. Moreover, the cost of RNA biomarker is much lower than protein biomarker because detecting each protein requires a specific antibody. Additionally, compared with DNA biomarkers, RNA biomarkers have the advantage of providing dynamic insights into cellular states and regulatory processes than DNA biomarkers. Besides, RNA has multiple copies in a cell, which delivers more information than DNA. Moreover, some RNAs with specific structures, such as circular RNA, have the potential to exist stably in plasma and/or serum.

Competing endogenous RNAs (ceRNAs) have been reported to regulate the distribution of miRNA molecules on their targets and thereby impose an additional level of post-transcriptional regulation. In particular, a muscle-specific lncRNA, linc-MD1, sponges miRNA-133 to regulate the expression of MAML1 and MEF2C, transcription factors that activate muscle-specific gene expression. It was found that HuR, which is under the repressive control of miRNA-133, is de-repressed due to the sponging activity of linc-MD1 on miRNA-133. This study, therefore, uncovered a feed forward positive loop involving muscle transcription factors, RNA binding proteins, miRNAs, and a lncRNA, that controls early phases of myogenesis. Interestingly, the levels of the muscle-specific lncRNA, linc-MD1 is strongly reduced in muscle cells of patients with Duchenne Muscular Dystrophy. In another study, it was reported that cardiac apoptosis-related lncRNA (CARL) could act as an endogenous miRNA-539 sponge to regulate PHB2 expression, mitochondrial fission and apoptosis. Modulation of their levels may provide a new approach for tackling apoptosis and myocardial infarction. Clearly, understanding this novel RNA crosstalk will lead to significant insight into gene regulatory networks and have implications in human development and disease.

Using both the functional leukocyte chemotaxis assay and the immunoassay ELISA, our studies demonstrated that the cardiac-derived Nourin peptide is rapidly released by ischemic heart tissue while it is still "viable" before cells are dead, as well as by necrotic hearts. Consistence results showing the "early" release of Nourin by ischemic hearts were demonstrated using various species (human, dog, rat and cow) as well as several models of ischemic injury to include AMI (necrotic), global cardiac arrest (necrotic), cardiopulmonary bypass surgery (reversible) and heart transplantation (reversible). The early release of Nourin by ischemic injury (FIG. 14) is clinically significant to abort infarction, save heart muscles and reduce myocardial injury. Unlike Troponin, Nourin was detected in fresh blood samples collected from ACS patients, as well as frozen samples stored at −70° C. for 3 years. The Nourin-based RNA network is an essential part of central dogma where RNA delivers genetic and regulatory information and reflects cellular states. RNA molecules are able to serve as non-invasive biomarkers for earlier disease diagnosis and level of risk, as well as monitor disease progression and prediction of drug therapy response on heart tissue. Compared to protein-based biomarkers, RNA biomarkers have more sensitivity and specificity as it can be tissue and disease specific.

It is known in the art that autophagy is a process involved in the clearance of damaged proteins and organelles and facilitates cellular health under various stress conditions including hypoxia, ischemia or oxidative stress. Reports indicate that cardiomyocyte autophagy develops in the heart during AMI and it is rapidly activated within 30 minutes after coronary ligation.

In one embodiment of the present invention, the Nourin molecular network composed of lncRNA-CTB89H12.4, hsa-miRNA-137, and FTLH-17 mRNA formyl substituted-MIINHNLAAINSHR (SEQ ID NO:16) as an autophagy-related RNA panel linked to cardiovascular ischemia to specifically identify ischemic cardiac events such as UA and AMI. It is disclosed that autophagy-related Nourin gene-based RNA network may be utilized as an early biomarker for cardiac ischemia. Specifically, there was a down-regulation of RNA-CTB89H12.4 after an AMI event, resulted in the up-regulation of hsa-miRNA-137 and activation of FTLH-17mRNA formyl substituted-MIINHNLAAINSHR (SEQ ID NO:16) with an increased translation and production of high levels of Nourin protein.

In another embodiment of the present invention, Nourin gene regulatory RNA molecular network is disclosed as additional biomarkers for AMI patients. Using the amino acid sequence of Nourin purified from human hearts during reversible ischemia, the Applicant has identified the Nourin gene-based RNA network through in silico data analysis after BLAST alignment with formyl substituted-MIINHNLAAINSHRSPGADGNGGEAMPGGGR (SEQ ID NO:15)

In another embodiment of the present invention, the Nourin gene-based RNA network expression level and pattern were analyzed in serum samples of AMI patients and healthy volunteers. The novel AMI-specific Nourin RNA-based integrated competing endogenous network is composed of:

(1) Ferritin heavy polypeptide 17 (FTLH-17) formyl substituted-MIINHNLAA INSHR (SEQ ID NO:16) gene for Nourin mRNA;
(2) homo sapiens microRNA-137 (hsa-miRNA-137) ggu-ccucuga cucucuucgg ugacgggua ucuugggugg auaauacgga uuacguuguu auugcuuaag aauacgcgua gucgaggaga guaccagcgg ca (SEQ ID NO:04) as a regulatory gene on FTLH-17; and
(3) long non-coding intergenic RNA-(lncRNA-CTB89H12.4) (SEQ ID NO:19) an autophagy-related gene for cardiac ischemia and regulates hsa-miRNA-137. Please refer to FIG. 15A-15I.

In another embodiment of the present invention, the utilization of Nourin integrated genetic epigenetic approach, CTB89H12.4 may be involved in epigenetic activation of miR-137 with subsequent modulation of FTLH-17 mRNA formyl substituted-MIINHNLAA INSHR (SEQ ID NO:16) with potential role in AMI pathogenesis. Standard qPCR-based validation of the network was done in serum from 69 AMI patients collected during the first 8 hours of chest pain and serum from 31 healthy control volunteers. AMI clinical diagnosis was confirmed by angioplasty analysis (presence of a blood clot) and elevation of Troponin I. The relation between the expression of Nourin RNA-based biomarker network and different clinicopathological factors was also explored, as well as the correlation between Nourin RNAs and the level of cardiac Troponin I assessed by Spearman correlation.

Compared with messenger RNAs presenting an average of 2,000 nucleotides long, mature miRNAs have a length of only ~21 to 23 nucleotides. Their subsequent targeting mechanisms show a great deal of complexity because each miRNA can target thousands of transcripts, and one mRNA can contain several target sites for different miRNAs. Currently there are over 2,000 known miRNAs in humans and more are constantly being discovered and added to the miRNA database, "miRBase". Several microRNAs have been shown to play major roles in myocardial ischemia. A previous study showed that microRNA-137 was down-regulated as the cardiomyocyte differentiates and proliferates, suggesting that miR-137 may play a critical role in cardiomyocyte regeneration. However, there has been no report yet on whether miRNA-137gguccucuga cucucuucgg ugacgggguau ucuugggugg auaauacgga uuacguuguu auugcuuaag aauacgcgua gucgaggaga guaccagcgg ca (SEQ ID NO:04) is differentially expressed in pathological cardiomyocytes such as AMI. miRNA-137 gguccucuga cucucuucgg ugacgggguau ucuugggugg auaauacgga uuacguuguu auugcuuaag aauacgcgua gucgaggaga guaccagcgg ca (SEQ ID NO:04) has an important role in controlling embryonic neural stem cell fate. The down-regulated expression of miR-137 was observed in glioma stem cells and it regulates neuronal maturation. Additionally, miRNA-137 gguccucuga cucucuucgg ugacgggguau ucuugggugg auaauacgga uuacguuguu auugcuuaag aauacgcgua gucgaggaga guaccagcgg ca (SEQ ID NO:04) is decreased in Alzheimer disease patients. The lncRNA-CTB89H12.4 [AC021078.1-201 (ENST00000499521.2)] is located on chromosome 5 and has 2 exons. lncRNA-CTB89H12.4 is also related to cardiomyocyte regeneration and angiogenesis.

In another embodiment of the present invention, the association of the Nourin gene-based RNA network with FTLH-17, miRNA-137 gguccucuga cucucuucgg ugacggguau ucuugggugg auaauacgga uuacguuguu auugcuuaag aauacgcgua gucgaggaga guaccagcgg ca (SEQ ID NO:04) and lncRNA-CTB89H12.4 is demonstrated along with their expression pattern and level in AMI patients and healthy volunteers.

It is preferred that a biomarker of ACS should fulfill a number of the following criteria; including:
(1) it should be tissue-specific and abundantly expressed in heart tissues;
(2) its expression level in circulation under normal conditions should be extremely low or undetectable;
(3) in ACS patients, it should be quickly released into the circulation from the damaged heart and stably expressed for some time with a long half-life within the sample;
(4) accessible using noninvasive methods;
(5) the capability of rapid and accurate detection with a high degree of sensitivity and specificity to the disease; and
(6) allows early detection with sensitivity to relevant changes in the disease.

Circulating miRNAs fulfill a number of these criteria. They are stable in blood circulation, they are often regulated in a tissue- and pathology-specific manner, and they can be detected with high sensitivity and specificity using sequence-specific amplification.

It has been hypothesized that necrosis of cardiac cells after AMI results in the leakage of miRNAs into the circulation and that miRNAs highly, and preferably, specifically expressed in the heart might be used to diagnose acute coronary events. The identification of stable circulating miRNAs launches a new generation of potential biomarkers, for which assays can be developed with relative ease, at a relatively low expense, but with potentially better specificity and sensitivity. These assays could easily be designed to combine a large number of circulating miRNAs, which could drastically change the use and interpretation of circulating biomarkers as we know them. At the moment, most studies are investigating the usefulness of individual miRNAs as biomarker for disease, but none of the prior art document has reported that a combination of multiple miRNAs like the Nourin RNA network, which are related to each other and cardiovascular ischemia, would provide greater accuracy with high sensitivity and specificity.

In another embodiment of the present invention, the preclinical study of the invention confirmed the following:
(1) the rapid release of Nourin by reversible ischemic hearts and
(2) necrotic tissues in many animal models of unstable angina and AMI;
(3) the biological activity of Nourin as a potent inflammatory mediator;
(4) purification of Nourin from human reversible ischemic hearts (patients undergoing bypass surgery);
(5) identification of amino acid sequence of Nourin released by human reversible ischemic hearts; and
(6) development of an antibody-based ELISA assay against the amino acid sequence of the Nourin epitope N-f-MII.

In another embodiment, the clinical application of the Nourin functional assay (leukocyte Chemotaxis) and the Nourin ELISA immunoassay (Nourin epitope f-MII) successfully established that:
(1) Nourin released by reversible ischemic hearts was detected in cardioplegic samples collected from patients undergoing open heart surgery and in serum and plasma samples collected from patients experiencing unstable angina while the heart muscles are still alive. A very important finding to permit early crucial therapy and save heart muscles from progressing to necrotic injury;
(2) Nourin is much earlier than the current gold standard Troponin in diagnosing unstable angina and AMI patients;
(3) Nourin can diagnose ACS patients immediately upon arrival to hospital ED without the required 3 to 6 hours wait for Troponin to be released by necrotic hearts at measurable levels in blood samples;
(4) Nourin can differentiate patients presenting to hospital ED with chest pain due to cardiac AMI from non-cardiac patients with also chest pain; and
(5) in comparison to the lack of stability of Troponin, Nourin is stable in ACS patients' samples kept frozen for three years.

The rapid and accurate diagnosis of unstable angina and heart attack patients presenting with chest pain to hospital ED and outpatient clinics play a significant role in saving patients' lives. Therefore, there is a crucial need for biomarkers that can quickly diagnose ACS patients while the myocardial tissue is still viable to permit early crucial therapy to save heart muscles and reduce myocardial necrosis and heart failure. Approximately 50% of AMI patients progress to heart failure. Therefore, the Applicants established that the autophagy-related Nourin gene-based RNA network as an early new biomarker for cardiac ischemia to save heart tissue.

In another embodiment of the present invention, an assay for the detection of one or more small molecules that are released as a result of certain heart disorders, including UA and AMI are disclosed. Unlike the Troponin assay currently in use as a marker of necrosis, the Nourin assay according to the invention uses a biomarker for reversible ischemia before death. The Nourin assay can be used to diagnose unstable angina patients presenting with chest pain to hospital ED and outpatient clinics, and also can be used to distinguish between cardiac patients (unstable angina and heart attack) and non-heart related symptoms of chest pain.

Therefore, in view of the above the Nourin assay, it can:
(1) identify unstable angina patients and reduce medical malpractice costs associated with missed heart attacks;
(2) complement and enhance the usefulness of the Troponin assay to rule in or out unstable angina and heart attack;
(3) unlike Troponin, it can immediately identify heart attack patients at arrival at hospital ED and eliminates the current required three to six hours of waiting; thus, allows crucial therapy to save heart muscles from dying; and
(4) also reduce unnecessary health care expenses by eliminating unnecessary hospital admissions of chest pain patients.

In another embodiment of the present invention, the aforementioned assay involves the use of at least one, and preferably three Nourin RNAs that are released as a result of cardiac ischemia including UA and AMI. More specifically, the invention provides for the use of the qPCR assay to detect a Nourin molecular network composed of lncRNA-CTB89H12.4 (SEQ ID NO: 19), hsa-miRNA-137 gguccucuga cucucuucgg ugacggguau ucuugggugg auaauacgga uuacguuguu auugcuuaag aauacgcgua gucgaggaga guaccagcgg ca (SEQ ID NO: 04), and FTLH-17 mRNA as an autophagy-related RNA panel linked to each other and to cardiovascular ischemia to specifically identify ischemic cardiac events such as UA and AMI.

In another embodiment of the present invention, the use of one or the three qPCR assays to detect Nourin RNAs that are released from cardiac tissue cells upon an episode of UA and AMI. The aforementioned RNAs, used alone or in combination, can thus be used to detect UA and AMI and to diagnose the cause of chest pain in cardiac patients. It is pertinent to note that, the RNAs can differentiate between patients experiencing or having recently experienced UA and AMI from those having chest pain, but not experiencing of having ACS.

In addition, at least one, and preferably three RNAs can be used to:
(1) detect subclinical or silent myocardial ischemia without infarction as well as low grade myocardial ischemia without cell death;
(2) identify disease risk and monitor progression; and
(3) predict drug therapy response on heart tissues in clinical trials.

In another embodiment of the present invention, it is evidenced that serum Nourin-based FTLH-17 mRNA, hsa-miRNA-137 gguccucuga cucucuucgg ugacggguau ucuugggugg auaauacgga uuacguuguu auugcuuaag aauacgcgua gucgaggaga guaccagcgg ca (SEQ ID NO: 04), and the Nourin protein measured by antibody to the Nourin polypeptide comprising of the epitope sequence N-f-MII are elevated in UA and AMI patients, while the level of lncRNA-CTB89H12.4 (SEQ ID NO: 19) dropped in AMI patients' samples. Based on these results, it is likely that miRNA-137-5p acggguauuc uuggguggau aau (SEQ ID NO:05) and miRNA-137-3p uuauugcuua agaauacgcg uag (SEQ ID NO:06) are also elevated in AMI patients' serum samples. Accordingly, combining the integrated genetic epigenetic approach of Nourin RNAs and the Nourin peptide could be a powerful panel of biomarkers for the early diagnosis of UA and AMI patients. For polygenic diseases such as AMI and a complex human serum, it is expected that a single gene biomarker approach may not suffice for the high-performance requirement of AMI diagnosis. Therefore, by enlisting multiple Nourin gene network and the Nourin peptide that are functionally linked to each other and to AMI functional networks, it will increase the chance of success than the simpler conventional single-marker approach (e.g., Troponin) as a useful diagnostic and disease monitoring biomarkers to complement protein-based biomarkers and classical risk factors for AMI diagnosis and prognosis.

In another embodiment of the present invention, using the standard chemotaxis functional assay and the ELISA immunoassay, clinical studies demonstrated that the level of Nourin was 3-fold higher in plasmas of ACS (UA and AMI) patients who presented to the ED within 1.5 to 3.5 hours after the onset of symptoms, while the standard cardiac biomarkers Troponin T and CK-MB were not detected. After clinical confirmation of ACS patients, Troponin was detected in AMI patients' samples and lasted for 36 hours. Nourin was also detected in same samples after 32 hours of onset of chest pain. Nourin level was not tested beyond the 32 hours. Additionally, an ELISA assay using antibodies developed specifically against Nourin's epitope N-f-MII moiety (hereinafter referred as "Nour001-A") demonstrated clinically:
(1) the detection of high levels of cardiac Nourin in frozen plasma samples (−70° C. for 3 years) collected from ACS patients within the first 8 hours of chest pain when Troponin I level was below the clinical-decision level (below 0.07 ng/ml) but were later confirmed the diagnosis of ACS; thus, Nourin ELISA distinguished ACS patients from non-cardiac patients with chest pain.
(2) the detection of high levels of cardiac Nourin in AMI patients' fresh plasma samples collected within the first 8 hours of chest pain when Troponin I levels were below the clinical-decision level (below 0.07 ng/ml) but were later confirmed the diagnosis of AMI; thus, Nourin ELISA distinguished AMI patients from non-cardiac patients with chest pain; and
(3) Nourin was not detected in plasma samples collected from non-cardiac patients also presenting to the ED within the first 8 hours of chest pain with negative Troponin I.

It is pertinent to note that a number of studies have indicated that the post transcriptional regulatory RNAs such as circulating non-coding micro RNAs (miRNAs) and long non-coding RNAs (lncRNAs) are potential biomarkers for AMI. Cardiac injury following AMI is known to increase the expression levels of circulating miRNAs such as miRNA-208a ugacgggcga gcuuuuggcc cggguuauac cugaugcuca cguauaagac gagcaaaaag cuuguugguc a (SEQ ID NO:07) miRNA-208a-5p gagcuuuugg cccggguuau ac (SEQ ID NO:08), miRNA-208a-3p auaagacgag caaaaagcuu gu (SEQ ID NO:09), miRNA-133 acaaugcuuu gcuagagcug guaaaaugga accaaaucgc cucuucaaug gauuugguccccuucaacca gcuguagcua ugcauuga (SEQ ID NO:01). miRNA-133a-5p agcugguaaa auggaaccaa au (SEQ ID NO:02), miRNA-133a-3p uuugguccccuucaaccagcug (SEQ ID NO:04), miRNA-1 ugggaaacau acuucuuuau augcccauau ggaccugcua agcuauggaa uguaaagaag uauguaucuc a (SEQ ID NO:10), miRNA-1-5p acauacuucu uuauaugccc au (SEQ ID NO:11), miRNA-1-3p uggaauguaa agaaguaugu au (SEQ ID NO:12) and miRNA-499-5p uuaagacuug cagugauguu u (SEQ ID NO:13), miRNA-499a-3p aacaucacag caagucugug cu (SEQ ID NO:14). The concentration of miRNA-208a, miRNA-133a, and miRNA-499 is elevated after ACS suggesting that circulating miRNA as diagnostic biomarkers in cardiovascular diseases. The cardiac-specific miR-208a is the most promising STEMI biomarker reported. The first three miRNAs (miRNA-208a, miRNA-133, miRNA-1) peak at 3 hours after AMI and miRNA-499 at 12 hours. Experimentally, the levels of miRNAs in plasma were highly comparable with cardiac Troponin levels in their rat model of isoproterenol-induced myocardial injury. They found miRNA-208 to be undetectable at baseline, increased after 3 hours of isoproterenol treatment, and significantly elevated up to 12 hours. MiRNA-208 was also found to be rapidly induced in rodent models of AMI where it was undetectable in sham-operated animals, increased at 30 minutes, peaked at 3 hours, and disappeared from plasma at 24 hours. In a subgroup of 20 patients with AMI of which blood samples were collected within 4 hours after the onset of symptoms, miRNA-208 was detected in all patients, whereas Troponin I was only detected in 85% of the patients, confirming the superior sensitivity of miRNA-208 at early time points. In a clinical setting the differences in time courses of release between specific miRNAs and Troponin I might be valuable. Especially in the consideration of the fact that the Troponin I levels begin to rise only 3 to 8 hours after AMI, diagnosis via biomarkers with a faster cardiac release, such as miRNA-208, miRNA-1, and miRNA-133, might be beneficial.

The release of miRNAs can be (a) actively secreted and these molecules are referred to as circulating miRNAs, (b) through a jab junction dependent mechanism and (c) as a consequence of cellular content release (macrovesicles, exosomes) following necrosis, for instances during an AMI. MicroRNAs play a pivotal role in a wide range of regulatory processes in the cells and in fact miRNAs deficiencies or excesses have been linked to a number of cardiovascular diseases. The apparent minimal effects of miRNAs under non-stress conditions as compared to their specific involvement during responses to AMI make miRNAs attractive diagnostic targets with little or no effects from normal non-stressed tissues. Similarly, the circulating lncRNA MIAT has been expressed in AMI patients and was able to distinguish STEMI from NSTEMI. However, the circulating lncRNA UCA1 decreased in AMI patients at two hours after the onset of symptoms. At this stage, certain miRNAs individually or in combination may possibly complement protein-based biomarkers and classical risk factors for AMI diagnosis and prognosis.

Circulating miRNAs are emerging as blood-based biomarkers for cardiovascular diseases since they offer many attractive features of biomarkers. They are stable in the circulation, their sequences are evolutionarily conserved, their expression is often tissue or pathology specific, and their detection is based on sequence-specific such as in the case of Nourin, features that are helpful in the development of sensitive and specific assays. In cardiovascular disease, "distinctive patterns" of circulating miRNAs have thus far been found for AMI, coronary artery disease (CAD), hypertension, heart failure (HF), and viral myocarditis (VM). Circulating miRNAs are found to be remarkably stable in plasma even under harsh conditions as boiling, low or high pH, long-term storage at room temperature, and in multiple freeze-thaw cycles. lncRNAs are also found to be present in circulation in a remarkably stable form, which can withdraw multiple freeze-thaw cycles and are resistant against RNase-mediated degradation.

Additional procedures to detect the circulating Nourin RNAs in cardiac patients' samples are by measuring exosomes and extracellular vesicles. In addition to the use of the standard qPCR, the Nourin-based RNA network can be detected in cardiac patients' samples using gold coated magnetic nanoparticles as a non-PCR based technique. For this Nanogold assay, the Nourin RNAs will be either extracted or measured directly in patients' samples without purification or pre-amplification. The Nanogold assay uses magnet beads coated with specific probe and gold nanoparticles to facilitate both RNA extraction and detection of expression using nanoparticles which seems to save time and cost. This assay will measure the Nourin RNA panel of markers in various sera samples. A citrate-capped gold nanoparticles (AuNPs) assay for the direct detection of unamplified Nourin-based RNA network in sera samples for the early diagnosis of AMI patients. The assay employs magnet nanoparticles (MNPs) functionalized with Nourin-based RNA-specific oligonucleotides for capturing and purifying the target RNA and AuNPs for detection. The method depends on colorimetric determination of unamplified RNA. In addition, Nourin-based RNA panel of markers can be detected in cardiac patients' samples using the technology provided commercially, for example by Multiplex miRNA assays measuring the Nourin-based RNA network via total circulating RNAs, Multiplex miRNA assays with FirePlex® particle technology enable simultaneous profiling of 65 miRNAs directly from small amounts of biofluid or FFPE, without RNA purification or pre-amplification. Assays can be customizable for the Nourin-based RNA panel of markers and suitable for both discovery and verification studies. Readout uses a standard flow cytometer. Additionally, sensor chip procedures can be used to detect the Nourin-based RNA network and the Nourin protein including and not limited to Nourin epitope f-MII.

The invention will be further explained by the following Examples, which are intended to purely exemplary of the invention, and should not be considered as limiting the invention in any way.

EXAMPLES

Example 1

Identify the Nourin Gene-Based RNA Network as Biomarkers for Cardiac Patients.

A combined approach of: (1) bioinformatic analysis (software analysis) using previous microarray studies was conducted and the results were related to our known Nourin peptide sequence to retrieve the Nourin-based RNAs; and (2) biomarker verification was conducted by determining the expression levels and pattern of Nourin RNAs in AMI patients' serum samples and compare them to healthy volunteers using standard qPCR.

To retrieve lncRNA-associated competing endogenous RNAs based on Nourin (Nourin ceRNAs) and to establish their clinical relevance in AMI patients based on previous microarray studies, the following three steps were conducted: (1) biomarker retrieval step to analyze ncRNA gene placement relative to AMI associated genes through public databases and to analyze lncRNA-miRNA interaction databases to lncRNA specific for AMI; (2) bioinformatic validation of the chosen lncRNA-associated competing endogenous RNAs related to AMI; and (3) using the standard quantitative real time PCR (qPCR) molecular assay to validate the chosen biomarker as a diagnostic marker for early detection of AMI in sera samples in comparison to the gold standard cardiac marker Troponin I.

Nourin RNA analysis was performed on serum samples collected from 69 AMI patients who were diagnosed with documented acute myocardial infarction and ongoing chest pain for 8 hours at the Emergency Department and 31 healthy normal volunteers with matching age and sex to the AMI patients' groups. AMI was diagnosed within the first 8 hours of chest pain on the basis of the presence of a blood clot in the coronary artery confirmed by angiography procedures and elevated serum Troponin I levels, in addition to clinical symptoms & history consistent with cardiac ischemia. The criteria for diagnosing AMI was in accordance with the American College of Cardiology/American Heart Association guidelines and reflected the clinical judgment of two experienced independent cardiologists. Patients were excluded from the study if they have a history of hepatitis, hepatic failure, end-stage renal failure, cardiomyopathy, congenital heart disease, bleeding disorders, previous thoracic irradiation therapy, autoimmune diseases, inflammatory diseases such as inflammatory bowel disease (IBD) and arthritis or malignant disease. Blood samples were obtained once within the first 8 hours of chest pain and were centrifuged and the serum was separated, aliquoted and stored immediately at −80° C. for further processing.

Blood samples were collected from 69 AMI patients and 31 healthy controls in primary blood collection tubes without clot activator and without anticoagulants such as EDTA or citrate (red-topped tubes). These blood samples were left at room temperature for a minimum of 30 min (and a maximum of 60 min) to allow complete blood clotting in the red-topped tubes. The clotted blood samples were then centrifuged at 1300×g at 4° C. for 20 min. The upper yellow serum was carefully removed, transferred to a polypropylene capped tube in 1 ml aliquots and stored at −80° C. until they are assayed by qPCR. All serum samples were labeled with a unique identifier to protect the confidentiality of the patients. None of the serum samples were allowed to thaw before analysis to minimize protein degradation and precipitation.

Biomarker validation using qPCR involved (1) extraction of the total RNA from serum samples (AMI and healthy); (2) generation of cDNA through reverse transcription; (3) measurement of cDNA using qPCR; and (4) evaluation of results by the plot curve analysis software of Rotor Gene to confirm specificities then amplification plot and data analysis. For the extraction of total RNA, including lncRNA, miRNA and mRNA from sera samples, miRNEasy RNA isolation kit (Qiagen, Hilden, Germany) was used according to manufacturer's instructions. The RNA samples were dissolved in 30 μl of nuclease-free water. The concentration of RNA was determined using a NanoDrop spectrophotometer (Thermo Scientific, USA). Total cDNA including cDNA for miRNA, mRNAs and lncRNA was prepared from sera samples and were loaded to Rotor Gene Thermal cycler (Thermo Electron Waltham, Mass.) using miScript II RT Kit (Qiagen, Germany) by adding 2 ul 10× miScript Nucleics Mix, 4 ul 5× miScript HiFlex Buffer, 1 ul miScript Reverse Transcriptase Mix and RNase free water to 2 ug RNA and the mixture was incubated for 60 minutes at 37° C. then for 5 minutes at 95° C.

Quantification of the expression pattern and levels of Nourin gene-based RNA network panel by qPCR included: lncRNA-CTB89H12.4 and FTLH-17 mRNA expression in sera samples were quantified by adding 10 ul 2×RT$^2$SYBR Green ROX qPCR Mastermix and QuantiTect SYBR Green PCR Kit, respectively, RT$^2$lncRNAq PCR Assay for RT$^2$ lncRNA qPCR Assay for Human CSNK1A1 (ENST00000499521) and Hs_FTHL17_1_SG QuantiTect Primer Assay (NM_031894), 2 ul template cDNA and RNase free water to a final volume of 20 ul Hs_ACTB_1_SG QuantiTect Primer Assay (NM_001101) was used as housekeeping gene to normalize our raw data as the invariant control for the samples, and compared with a reference sample. The PCR program for relative lncRNA-CTB89H12.4 quantification was conducted as follow: firstly, denaturation at 95° C. for 10 min; followed by 45 cycles of denaturation for 15 seconds at 95° C.; then annealing for 30 seconds at 55° C. and extension for 30 seconds at 70° C.

To quantify the expression of hsa-miR-137 in the different sera samples, we used miScript SYBR Green PCR Kit (Qiagen/SA Biosciences Corporation, Frederick, Md.) by adding 10 ul 2× miScript SYBR Green PCR Master Mix, 2 ul 10× miScript Universal Primer, 2 ul 10× miScript Primer Assay for either Hs_miR-137_1 miScript Primer Assay targets mature miRNA: hsa-miR-137 (MIMAT0000429: 5'UUAUUGCUUAAGAAUACGCGUAG) or RNU6B, 2 ul template cDNA and RNase free water to a final volume of 20 ul. All the PCR primers were purchased from (Qiagen, Germany Md.). The real-time cycler was programmed for relative quantification of FTLH-17 mRNA and Hsa-miRNA-137 as follows: initial activation step for 15 min at 95° C. to activate HotStarTaq DNA Polymerase. 40 cycle of PCR were performed under the following conditions; 15 seconds at 94° C., 30 seconds at 55° C. and 30 seconds at 72° C. for denaturation, annealing and extension respectively. Each reaction was carried out in triplicate. Relative quantification of RNA-based biomarker panel expression was calculated using Leviak method RQ=$2^{-\Delta\Delta Ct}$ method. The threshold cycle (Ct) value of each sample was calculated using the Rotor Gene real time PCR detection system (Qiagen, Hilden, Germany). Any Ct value more than 36 was considered negative. The results were analyzed by the plot curve analysis software of Rotor Gene. Amplification plots and Tm values were analyzed to confirm the specificities of the amplicons for SybrGreen-base amplification.

For Nourin RNA's stability in the collected blood samples, we have stored sera samples at −70 for about (4 to 6 months). Sera samples were processed within half an hour after collection and aliquoted to minimize freeze thaw cycle. We have used spin columns with small pore sizes in an attempt to concentrate serum RNA before the precipitation step and have checked the concentration and purity of RNA using U/V spectrophotometer. Real time PCR was done after RNA extraction at the same day. Mean delta CT for housekeeping genes were 24 indicating average RNA expression. In general, RNAs are stable in serum for 2 years. We have investigated miRNA and long non-coding RNA which are already most stable forms of RNA. In general, miRNAs are detected in serum or plasma in a remarkable stable form and can withstand repetitive freezing and thawing cycles. In addition, circulating miRNAs are resistant against RNase-mediated degradation.

Measurement of cardiac Troponin I was conducted in serum samples collected from AMI patients and healthy control samples. The manufacturer of cardiac Troponin I is Siemens (adiva contour). The cardiac Troponin I assay is a 3-site sandwich immunoassay using direct chemillumenscence. The units for the measurements are ng/ml and the 99$^{th}$ percentile upper reference limit of a range 0.04 ng/ml.

All statistical data were executed using SPSS 22 Mann Whitney, independent t test, and chi-square test were used as appropriate to complete comparisons. To characterize the predictive value of the selected RNA-based biomarker panel for AMI, the Receiver Operating Characteristic (ROC) curve was carried out. The Spearman correlation was performed to detect the associations between RNA-based biomarker network expression and clinicopathological parameters. Two-tailed P value of 0.05 or less was supposed to be statistically significant.

Additional procedures to detect the circulating Nourin RNAs in cardiac patients' samples are by measuring exosomes and extracellular vesicles. Furthermore, in addition to the use of the standard qPCR, the Nourin-based RNA network can be detected in cardiac patients' samples using the gold coated magnetic nanoparticles as a non-PCR based technique. For this Nanogold assay, the Nourin RNAs will be either extracted or measured directly in patients' samples without purification or pre-amplification. This assay will measure the Nourin RNA panel of markers in various sera samples. In addition, Nourin-based RNA panel of markers can be detected in cardiac patients' samples using the technology provided commercially, for example by Multiplex miRNA assays measuring the Nourin-based RNA network via total circulating RNAs, Multiplex miRNA assays with FirePlex® particle technology enable simultaneous profiling of 65 miRNAs directly from small amounts of biofluid or FFPE, without RNA purification or pre-amplification. Assays can be customizable for the Nourin-based RNA panel of markers and suitable for both discovery and verification studies. Readout uses a standard flow cytometer. Additionally, sensor chip procedures can be used to detect the Nourin-based RNA network and the Nourin protein including and not limited to Nourin epitope N-f-MII.

Furthermore, the Point-of-Care (POC) procedures can be used to rapidly within 15 minutes detect in cardiac patients' samples the circulating Nourin RNAs including RNA FTLH-17 mRNA, miRNA-137 and lncRNA-CTB89H12.4 as well as the Nourin epitope N-f-MII. The POC diagnostics has been emerged as a promising real-world application. The POC ecosystem is evolving faster than ever and new technology has to fit into a broader landscape. Some of the main advantages of POC diagnostic device include the use of smaller sample volume, lower test costs and faster turn-around-times i.e., 15 minutes vs, 4 hours to 24 hours for PCR. Beside its rapid and precise response, its portability, low cost and non-requirement of specialized equipment are important advantages. The challenge is that the POC devices use smaller sample volumes to achieve the same detection limit as standardized laboratory equipment. It requires the integration of assay chemistry, fluidics, hardware and software.

A POC device can use a chip-based technology to examine different analytes in various samples including blood, urine and tissue biopsies. Microfluidics and biosensor can use numerous materials such as glass, silicon, polymer, and paper for the fabrication of microfluidics-based POC devices along with their wide range of biosensor applications. Recent development in nanomaterials, device design, and microfabrication technologies have made it possible to obtain POC devices with enhanced sensing characteristics. Breakthroughs such as the recently published method of 3D printing microfluidics lab-on-a-chip devices could help lead to cheaper mass-production of diagnostic devices. The use of smartphones paired to microfluidics could enable an increased range and ability of POC testing, with the development of devices such as the TRI analyzer on the horizon, it is possible to achieve limits of detection that are comparable to those obtained for the same assay measured with a conventional laboratory microplate reader, demonstrating the flexibility of the system to serve as a platform for rapid, simple translation of existing commercially available bio sensing assays to a POC setting. POC portable devices identification method can be based on microarray platform require extensive testing and validation comparing the outcome with more traditional methods of detection. Thus, the high-performance RNA-detection methods for all types of clinically relevant RNAs (mRNAs, miRNAs and lncRNAs) are based on molecular-biology techniques including and not limited to qPCR, microarrays, nanoparticles, microfluidics and biosensor.

Example 2

Retrieve Molecular Biomarkers Relevant to AMI and Related to the Nourin Peptide Sequence.

Bioinformatic analysis was done to retrieve biomarkers relevant to AMI and related to the Nourin peptide sequence based on previous microarray studies. The bioinformatic analysis included a number of blast programs to retrieve relevant genes to the Nourin peptide sequence. We have retrieved Ferritin heavy polypeptide 17 (FTLH-17) gene after BLAST alignment 100% with the Nourin-1 peptide sequence (U.S. Pat. No. 7,659,091 B2) formyl substituted-MIINHNLAAINSHRSPGADGNGGEAMPGGGR (SEQ ID NO:15). Ferritin is the major intracellular iron storage protein in prokaryotes and eukaryotes. It is composed of 24 subunits of the heavy and light ferritin chains. Variation in ferritin subunit composition may affect the rates of iron uptake and release in different tissues. A major function of ferritin is the storage of iron in a soluble and nontoxic state. We have then identified the Nourin gene-based RNA network through in silico data analysis. For clinical validation of the chosen Nourin gene-based RNA network as diagnostic biomarkers for early diagnosis of AMI, we have investigated the serum gene network expression of Nourin FTLH1 mRNA, hsa-miR-137 and long non-coding RNA-CTB-89H12.4 in AMI patients' serum samples collected within the first 8 hours of chest pain as well as in healthy control samples.

Figure 3:
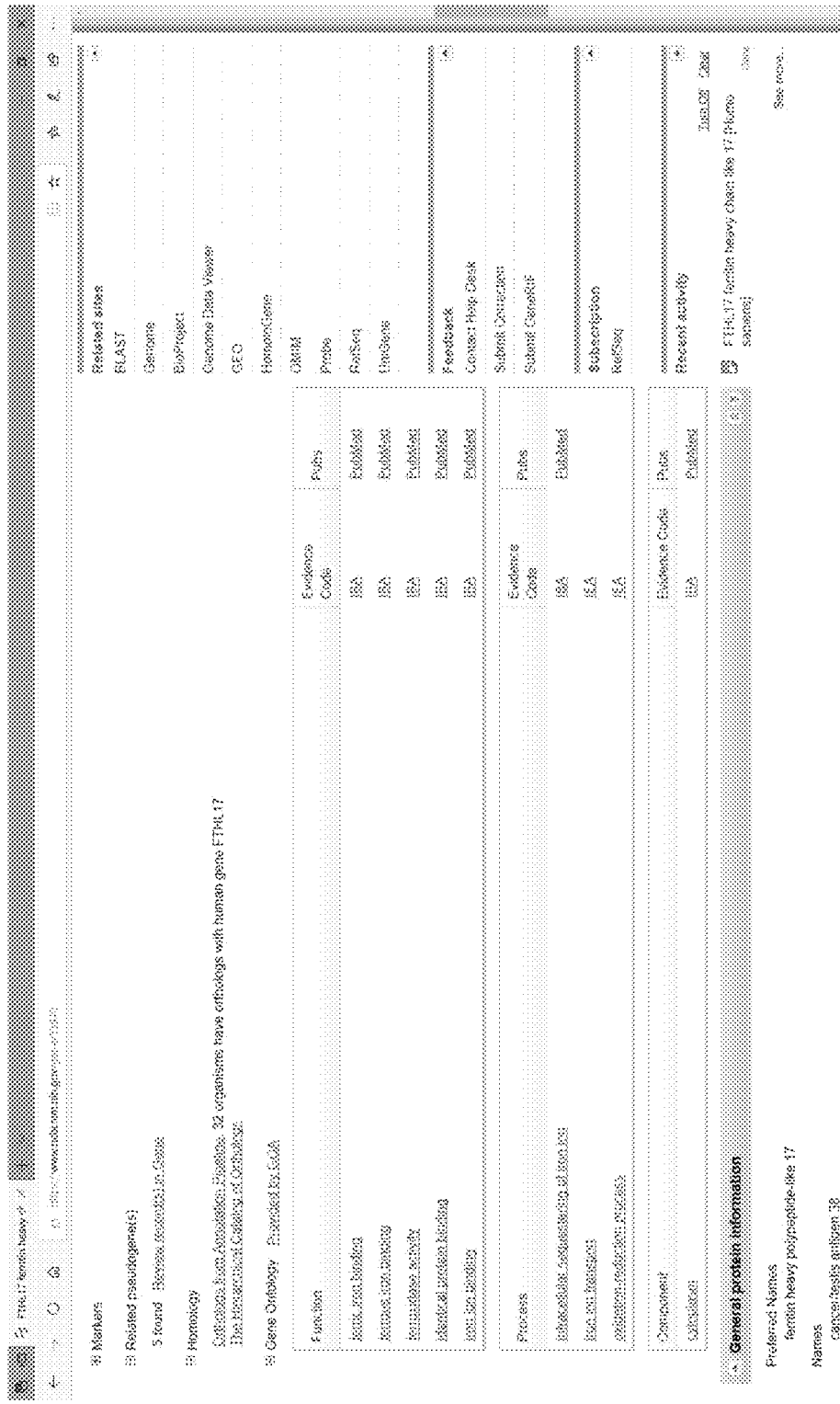
FIG. 3 indicates a snapshot showing gene ontology of FTLH17 mRNA. https://www.ncbi.nlm.nih.gov/gene/53940
Figure 4:
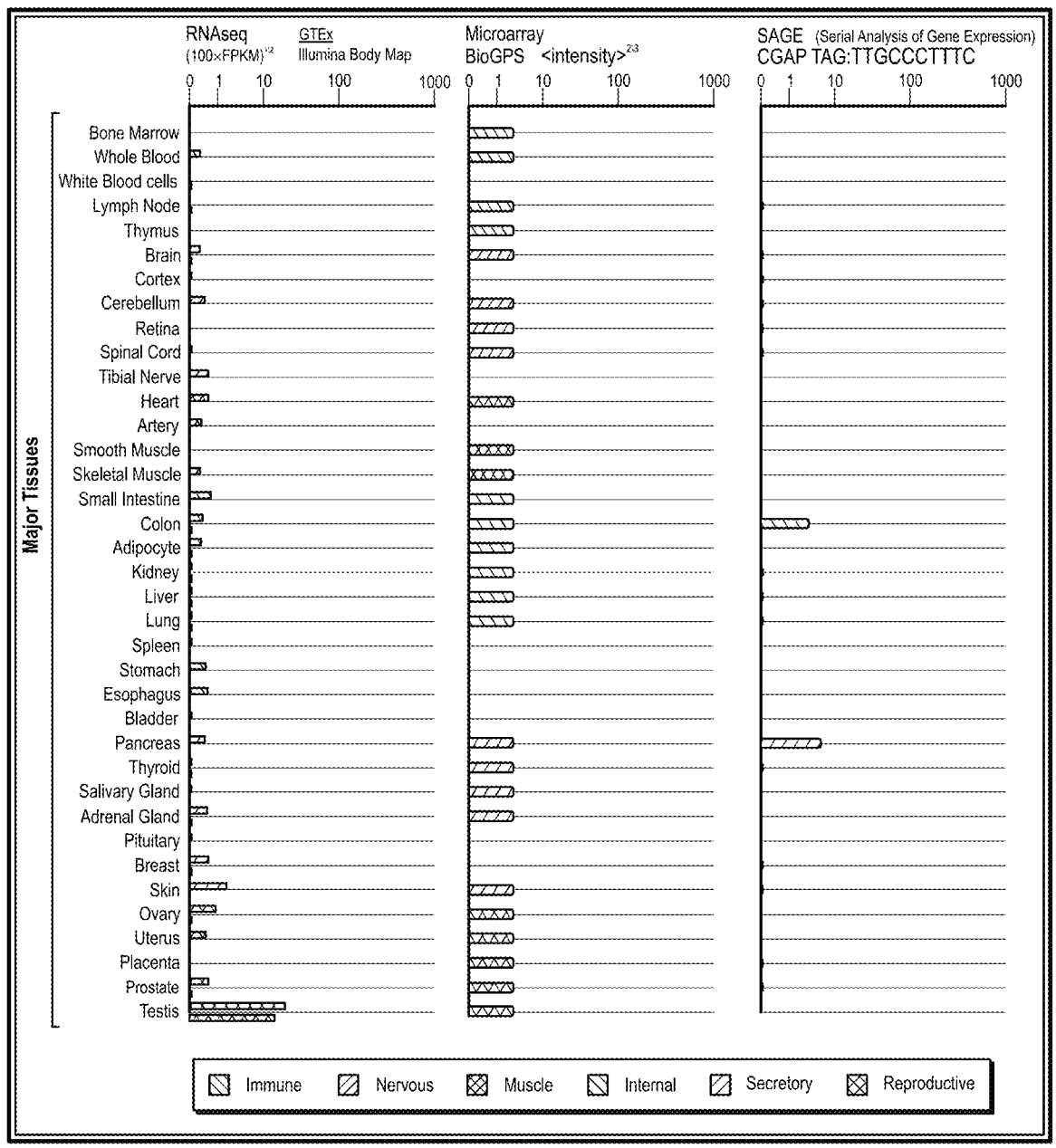
FIG. 4 indicates a snapshot showing minimal gene expression of FTLH17 mRNA in normal tissues confirming the low level of Nourin FTLH17 mRNA and Nourin protein detected in serum and plasma samples collected from healthy volunteers. https://www.genecards.org/cgi-bin/carddisp.pl?gene=FTHL17&keywords=FTHL17
Figure 5:
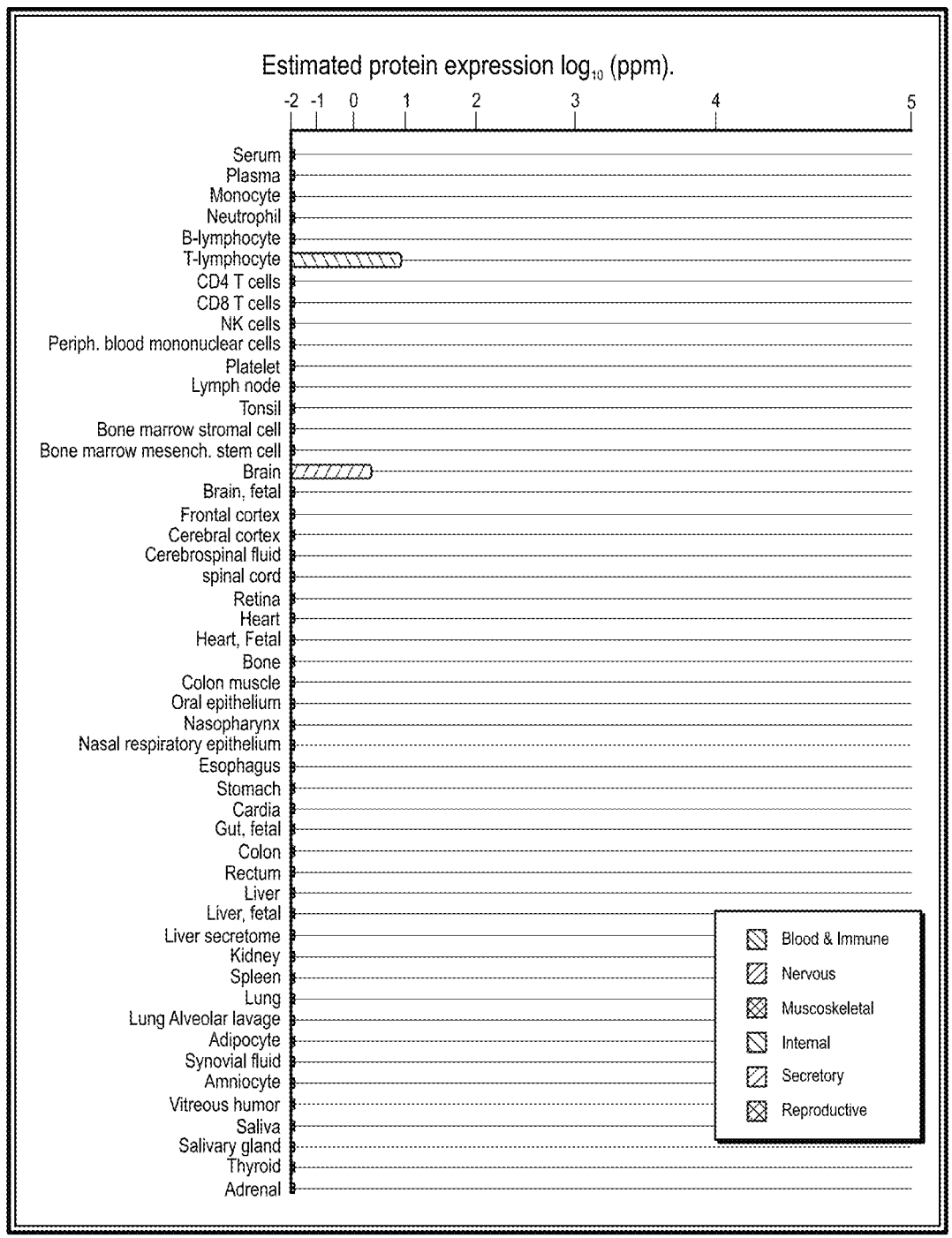
FIG. 5 indicates a continuation of the snapshot showing minimal gene expression of FTLH17 mRNA in normal tissues confirming the low level of Nourin FTLH17 mRNA and Nourin protein detected in serum and plasma samples collected from healthy volunteers. https://www.genecards.org/cgi-bin/carddisp.pl?gene=FTHL17&keywords= FTHL17

To retrieve the lncRNA-associated competing endogenous RNAs based on Nourin sequence & its relevant to AMI based on previous microarray studies, we conducted the following four blast programs to retrieve the relevant gene to the Nourin peptide sequence: (1) using Atlas database retrieving target gene involved that is relevant to the Nourin peptide. we have selected the FTLH17 gene after BLAST alignment with the Nourin sequence formyl substituted-MIINHNLAAINSHRSPGADGNGGEAMPGGGR (SEQ ID NO:15) corresponding to Nourin-1 (U.S. Pat. No. 7,659,091 B2) with sequence identity 100% and confirmed by gene ontology which revealed that FTLH17 gene is related to autophagy and cardiac ischemia (reversible and irreversible cardiac ischemia as seen in UA and AMI patients) as illustrated in FIG. 1, FIG. 2 and FIG. 3; (2) we then confirmed the low expression of FTLH17 mRNA in normal tissues (FIG. 4 and FIG. 5). This low expression of FTLH17 mRNA in normal heart was reported in by two techniques out of three. For normal kidney, one technique proved low expression and other 2 techniques negative. Together, FTLH17mRNA is expressed at low level in normal heart, but more than other tissues (FIG. 4 and FIG. 5); (3) next, we used Diana database to retrieve miRNA-137 that acts as epigenetic regulator of FTLH-17 mRNA and by performing pathway enrichment analysis we confirmed that miRNA-137 is related to autophagy and cardiac ischemia (FIG. 6); and finally, (4) we have selected lncRNA-CTB89H12.4 that acts as miRNA-137 sponge through Starbase database (FIG. 7).

Example 3

Differentiation of AMI Patients with Chest Pain from Healthy Controls using the Nourin FTLH-17 mRNA gene, long non-coding intergenic RNA-(lncRNA-CTB89H12.4) and homo sapiens microRNA-137 (hsa-miRNA-137).

After identification of the Nourin gene-based RNA network retrieved through in silico data analysis, we determined the Nourin RNA expression pattern and level in 69 AMI patients presenting to hospital ED with chest pain within 8 hours after onset of symptoms and 31 healthy volunteers as an important first step to determine the biomarker signatures of Nourin that will be effective in AMI detection. Specifically, we investigated the Nourin gene-based RNA network expression as a novel AMI-specific RNA-based integrated competing endogenous network composed of ferritin heavy polypeptide 17 (FTLH-17 mRNA) gene, long non-coding intergenic RNA-(lncRNA-CTB89H12.4) and homo sapiens microRNA-137 (hsa-miRNA-137) selected by in silico data analysis. Standard RT-qPCR-based validation of the network was used and the relation between the expression of Nourin RNA-based biomarker network and different clinicopathological factors was explored. The correlation between Nourin RNAs and the level of cardiac Troponin I was assessed by Spearman correlation.

Figure 8:
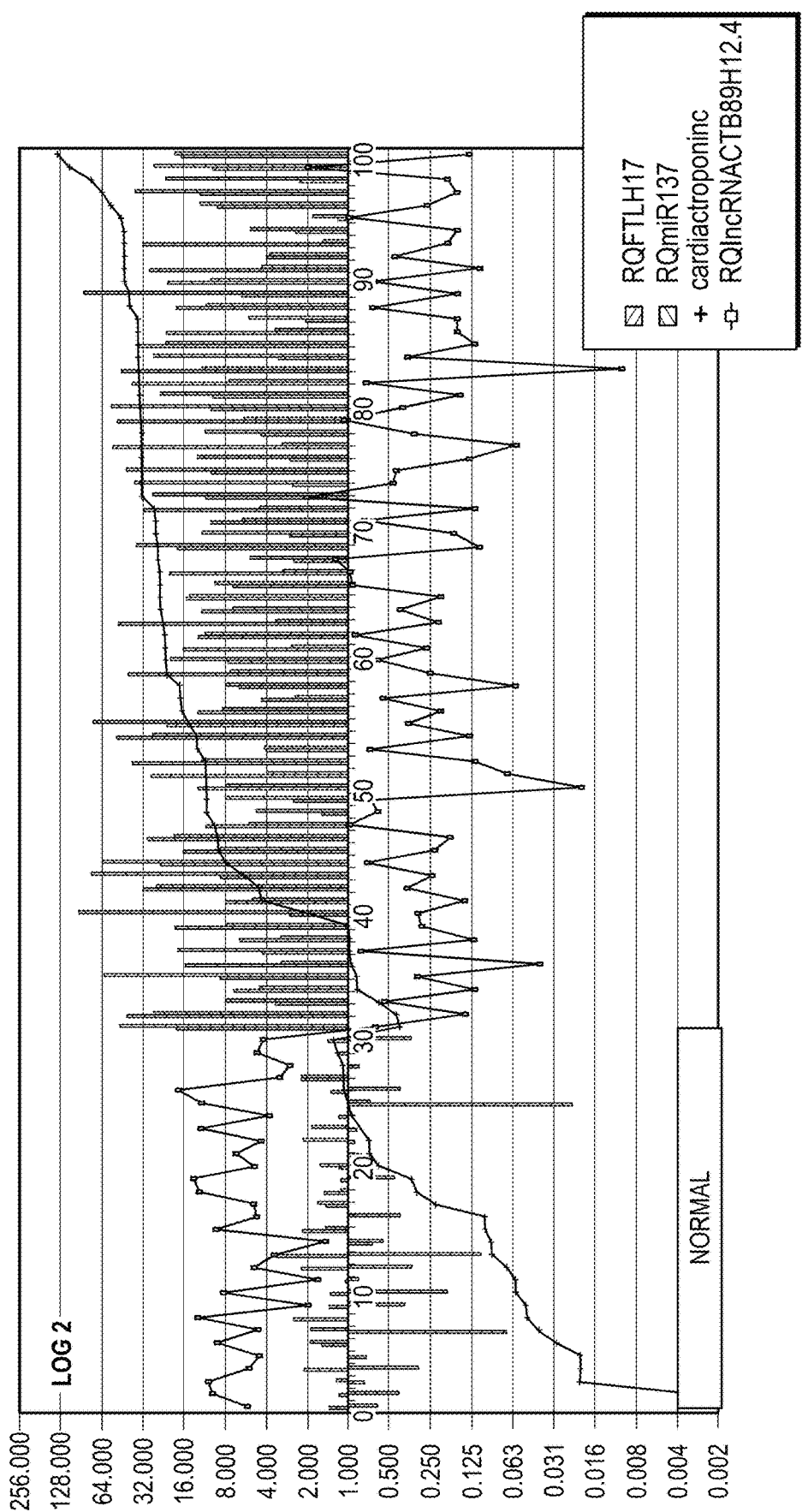
FIG. 8 indicates the expression pattern and level of the Nourin-based molecular biomarker panel of FTLH-17 mRNA, hsa-miRNA-137 and lncRNA-CTB89H12.4 in comparison to Troponin I measured in the same serum samples collected from AMI patients and healthy volunteers. Results revealed that the two-log analysis of the three RNAs-based biomarker network (long non-coding intergenic RNA-(lncRNA-CTB89H12.4), homo sapiens microRNA-37 (hsa-miRNA-137), and FTLH-17 mRNA, had high sensitivity and specificity for discriminating AMI patients from healthy controls. While the AMI group had a higher expression of FTLH-17 mRNA and hsa-miRNA-137 as well as elevated levels of Troponin I in comparison to the healthy control group, there is concomitant lower expression of lncRNACTB89H12.4 in AMI patients and higher expression in the healthy control group.
Figure 9:
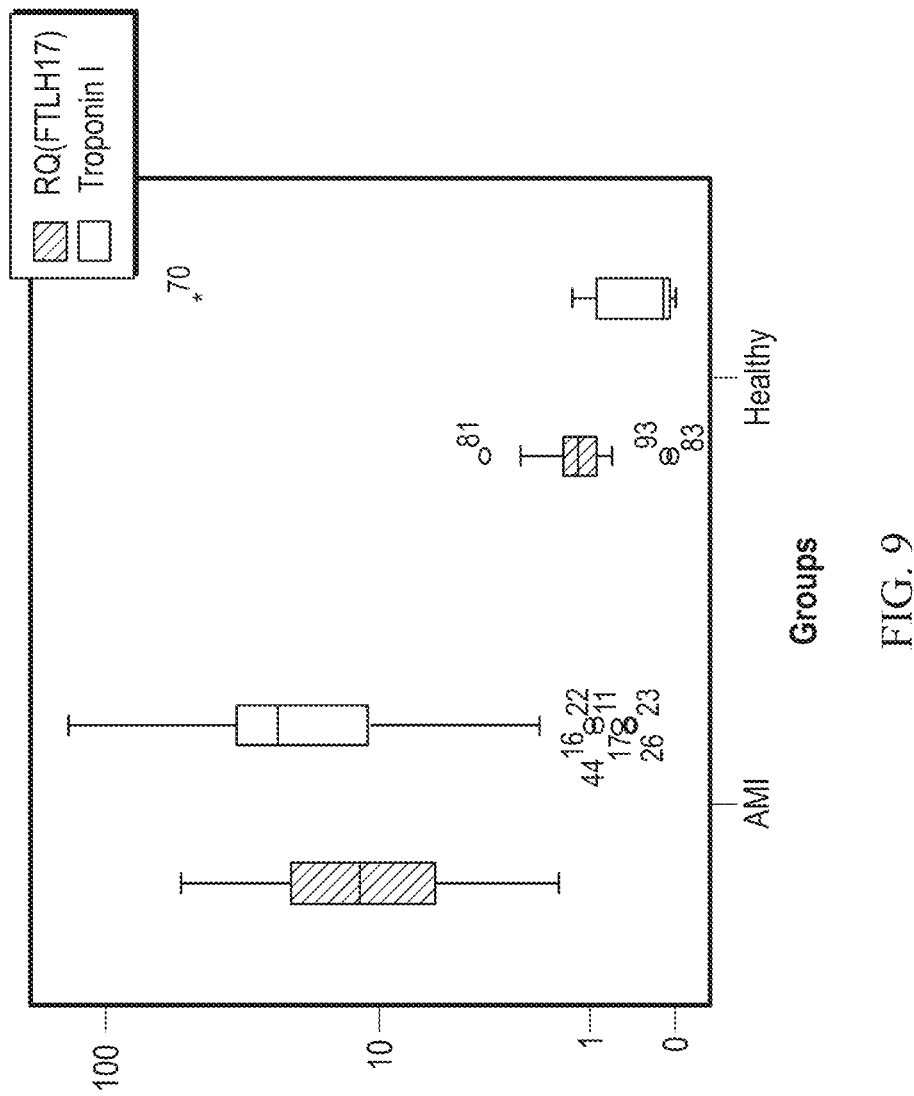
FIG. 9 indicates the expression level of the Nourin-based molecular biomarker FTLH-17 mRNA in comparison to Troponin I measured in serum samples of AMI patients and healthy volunteers. Highly significant difference by the independent t test ($P<0.001$).
Figure 10:
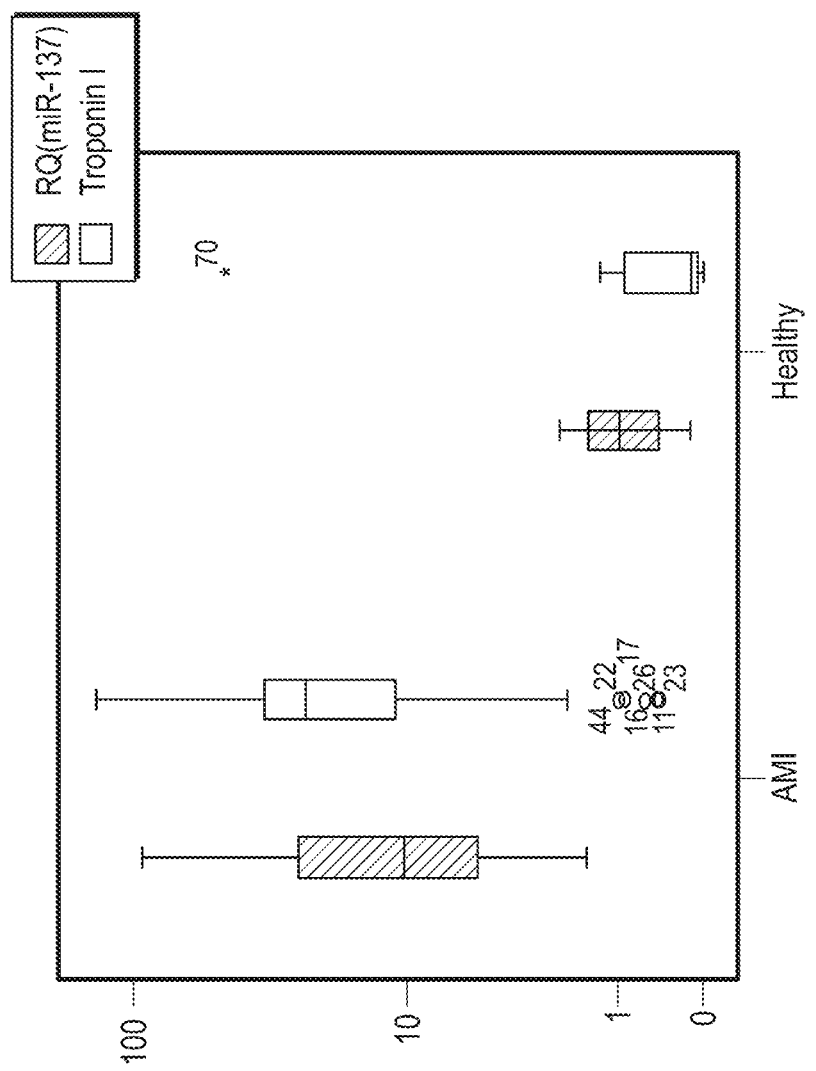
FIG. 10 indicates the expression level of the Nourin-based molecular biomarker hsa-miRNA-137 in comparison to Troponin I measured in serum samples of AMI patients and healthy volunteers. Highly significant difference by the independent t test (P<0.001).
Figure 11:
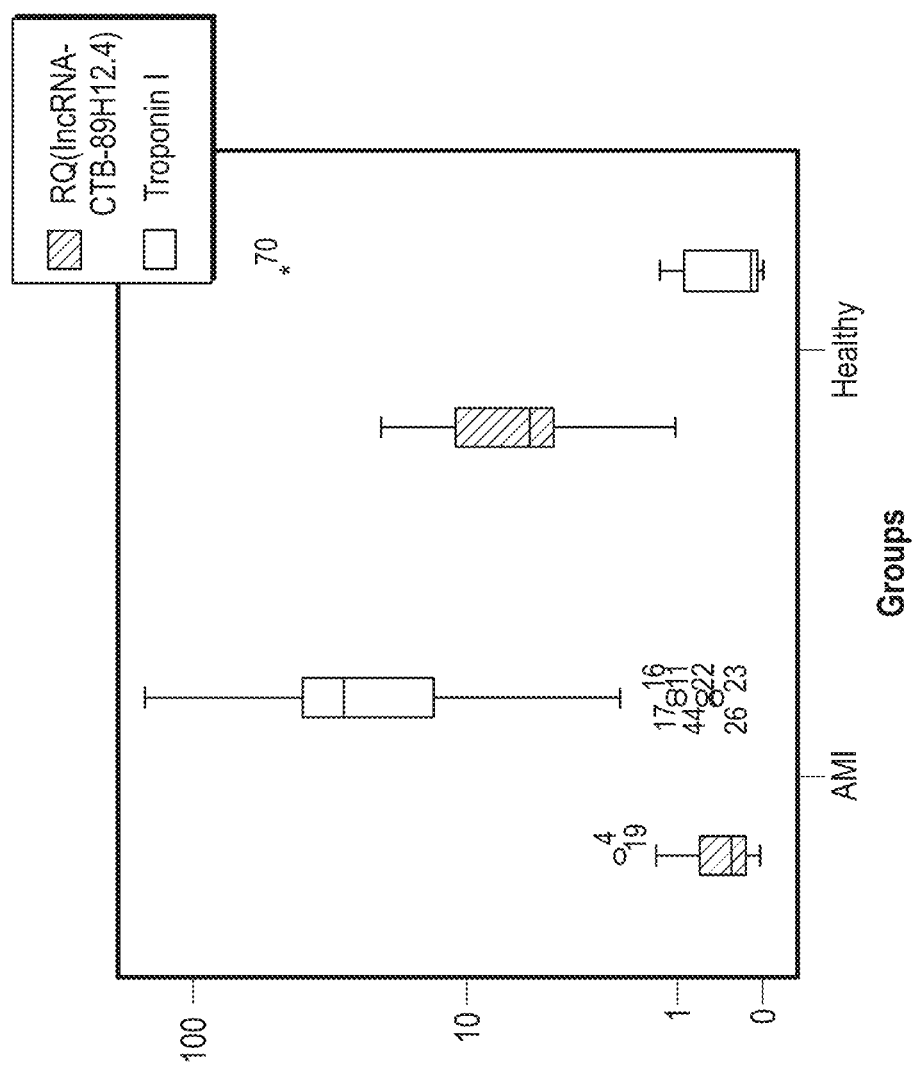
FIG. 11 indicates the expression level of the Nourin-based molecular biomarker lncRNA-CTB89H12.4 in comparison to Troponin I measured in serum samples of AMI patients and healthy volunteers. Highly significant difference by the independent t test (P<0.001).

Results revealed that the expression pattern and level of the Nourin-gene RNA network composed of long non-coding intergenic RNA-(lncRNA-CTB89H12.4), homo sapiens microRNA-37 (hsa-miRNA-137), and FTLH-17 mRNA had high sensitivity and specificity for discriminating AMI patients from healthy controls (FIG. 8). The recorded average of onset of chest pain is 6.52 hours. There was no significant difference detected between the expression of serum Nourin RNAs and the distribution of sex, smoking, diabetes mellitus, cholesterol, hypertension and the type of treatment in the AMI group. Furthermore, the RNA-based network and Troponin I were detected in clinically documented AMI patients with anterior STEMI, inferior STEMI as well as Non-TEMI (NSTEMI). There was a significant correlation, however, between Nourin FTLH-17 mRNA (FIGS. 9) and microRNA-37 (hsa-miRNA-137) (FIG. 10) and the level of the standard cardiac marker, Troponin I with concomitant negative correlation between lncRNA-CTB89H12.4 (FIG. 11) and cardiac Troponin I level in AMI and healthy serum samples. Since there was a correlation between Nourin RNA molecular biomarker panel and cardiac Troponin I level in both AMI serum samples, a combined assay that uses the Nourin protein (e.g., epitope N-f-MII) and the Nourin multiple genes that are functionally linked to each other and to AMI molecular networks, increases the chance of a higher success to accurately diagnose AMI patients than the simpler conventional single-marker approach for Troponin I. The circulating transcriptome of the Nourin gene-based RNA network expression has been revealed as a potential class of non-invasive biomarker with high specificity and sensitivity for early detection of AMI. We proposed an integrative approach between differential FTLH-17 gene expression with the selected epigenetic regulators and this approach has generated an interesting new Nourin-based molecular biomarker panel (lncRNA-CTB89H12.4, hsa-miRNA-137, and FTLH-17 mRNA) for the early diagnosis of AMI patients presenting with chest pain to hospital ED and outpatient clinics. Since the Nourin RNAs are stable, specific and abundantly expressed in ischemic hearts, they will be an added value to the Nourin protein assays. In general, RNA biomarkers have more sensitivity and specificity with much less interference in serum samples and that the qPCR assay enables traces of RNA sequences to be amplified and thus captured specifically with high sensitivity. Moreover, the cost of RNA biomarker is much lower than protein biomarker because detecting each protein requires a specific antibody. The ROC curves analysis and the area under the curve (AUC) values were used to estimate the diagnostic value of our selected RNAs to differentiate AMI from healthy controls. The results implied that hsa-miRNA-137 and lncRNA-CTB89H12.4 are the most effective biomarkers for differentiating AMI patients from healthy people. The best discriminating cutoff values of hsa-miRNA-137, lncRNACTB89H12.4 and FTLH-17 mRNA were 2.29, 3.36 and 3.83, respectively with sensitivities of 98.6%, 97.1% and 82.6%, respectively. Collectively, we believe that the diagnostic accuracy for AMI detection would be improved by a concurrent measurement of serum lncRNA-CTB89H12.4, miRNA-137, and FTLH-17 mRNA to approximately 100% sensitivity and 98% accuracy in the present study. This result indicates that these thresholds could be used to discriminate AMI patients from healthy subjects.

Example 4

Confirmation of Prior Results Using the Cardiac-Derived Nourin Protein.

Previous studies by the Applicant had shown that the 3 KDa Nourin-1, is released shortly after an ischemic cardiac event, e.g., UA and AMI. Those studies relied on either a leukocyte functional chemotaxis assay or an immunoassay using (a) monoclonal sera raised against the native full-length Nourin-1 protein; and (b) polyclonal sera raised against a short peptide sequence derived from the N-terminus of Nourin-1 (Nour001-A) generated in mice. The amino acid sequence formyl substituted-MIINHDDERKC (SEQ ID NO:17) was chemically synthesized and purified using HPLC. This peptide was conjugated to KLH using a proprietary method of Precision Antibody (Columbia, Md.), and mice were immunized. Tail bleeds were collected for determination of antibody titer at three weeks, and final cardiac bleeds were performed at four weeks to collect final sera. The collected sera were tested for specificity of binding to the immunogen as follows. Diluted sera were combined with a control peptide (MIINHDDERKC; SEQ ID NO:18) in excess to bind and remove antibodies in the sera that bind to any portion of the immunogen other than a portion that includes the formyl-methionine. The "cleared" sera were tested against a screening antigen having the sequence formyl substituted-MIINHDDERKC (SEQ ID NO:17). From a comparison of the sequences, the screening antigen shows identity to the immunogen only at the N-terminal five residues. Results of an ELISA with the "cleared" sera contained antibodies that specifically bound to the formylated N-terminal sequence.

Figure 12:
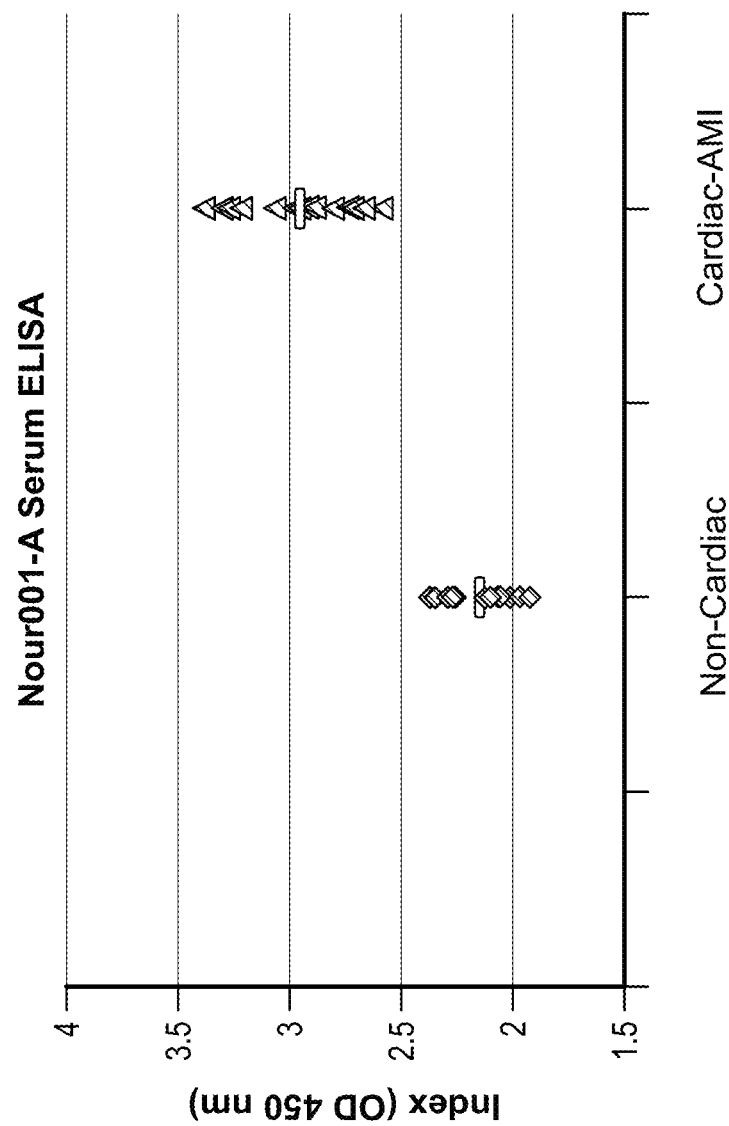
FIG. 12 indicates the differential level of the Nourin protein measured with the ELISA immunoassay in Cardiac-AMI patients presenting to hospital ED with chest pain and non-cardiac patients also complaining of chest pain. The ELISA immunoassay measured antibodies (hereinafter referred to as "Nour001-A") developed against Nourin polypeptide comprising of the epitope sequence N-f-MII moiety. Troponin negative (−) samples (labeled "Non-Cardiac) showed an average OD reading of approximately 2.2, whereas the Troponin positive (+) samples (labeled "Cardiac AMI") showed an average OD reading of approximately 2.9, with no overlap between individual samples of the two types. The Nour001-A antibody assay showed a statistical significance difference (P=0.0001) between samples from Cardiac-AMI patients and Non-Cardiac patients with chest pain. When the same samples were stored for one month at −20° C. then thawed and subjected to the same ELISA test procedure, the data was similar to and confirmed the results obtained using fresh samples, showing a difference between Troponin (+) samples and Troponin (−) samples. In this repeat frozen-sample study, Troponin (+) samples showed an average OD of approximately 2.4, whereas the Troponin (−) samples showed an average OD of approximately 1.8. The lack of stability of Troponin as a significant drawback to its use as a marker for AMI in stored samples, is overcome by the Nourin assay. Thus, the Nour001-A antibody binding profile correlates well with Troponin level profile. As such, the Nour001-A antibody is well suited as a detection reagent for AMI and can differentiate between patients suffering AMI and patients complaining of chest pain, but not suffering AMI. The Nour001-A antibody, thus, can be used in diagnostic assay to differentiate AMI patients from non-cardiac.

Using the functional leukocyte chemotaxis assay and the ELISA immunoassay (Nour001-A), clinical studies demonstrated that (1) the level of Nourin was 3-fold higher compared to healthy volunteers in plasmas of ACS (UA and AMI) patients who presented to hospital ED within 1.5 to 3.5 hours after the onset of symptoms, while the standard cardiac biomarkers Troponin T and CK-MB were not detected. After clinical confirmation of ACS patients, Troponin T was detected and it was persistent for 36 hours. Nourin which was also detected in samples after 32 hours; (2) the detection of high levels of cardiac Nourin in frozen plasma samples (−70° C. for 3 years) collected from ACS patients (UA and AMI) within the first 8 hours of chest pain when Troponin I levels were below the clinical-decision level (below the heart attack cut off of 0.07 ng/ml) but were later confirmed the diagnosis. The Nour001-A antibody assay showed a statistical significance difference (P=0.012) between samples from ACS patients and other non-cardiac patients with chest pain; (3) the detection of high levels of cardiac Nourin in AMI patients' fresh plasma samples collected within the first 8 hours of chest pain when Troponin I levels are below the clinical-decision level (below the heart attack cut off of 0.07 ng/ml) but were later confirmed AMI diagnosis demonstrating that Nourin is an earlier marker than Troponin I (FIG. 12). When the same samples were stored for one month at −20° C. then thawed and subjected to the same ELISA test procedure, the data obtained was similar to the results obtained using fresh samples, showing; (4) Nourin was not detected in plasma samples collected fresh from non-cardiac patients also presented to hospital ED within the first 8 hours of chest pain with negative Troponin I (FIG. 12). Thus, the Nour001-A antibody is useful in diagnosing patients suffering cardiac ischemic event and could differentiate between ACS (AMI and UA) samples taken from patients experiencing chest pain from chest pain patients but not suffering AMI or UA. Furthermore, the Nour001-A antibody assay distinguished AMI patients from non-cardiac patients using fresh and frozen samples.

Example 5

Up-Regulation of Nourin gene-based RNA Network and Protein in AMI.

Figure 13:
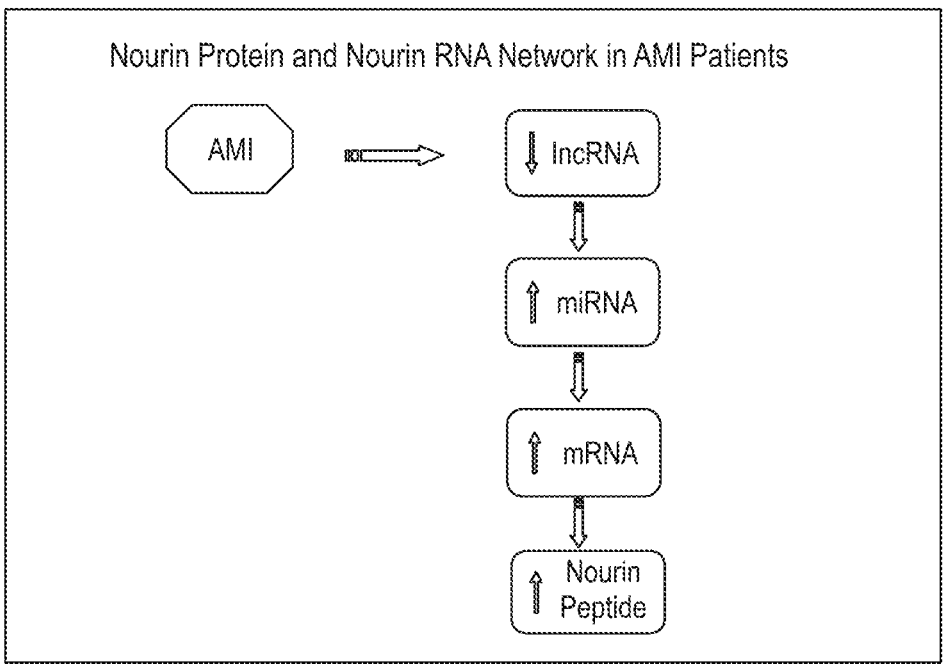
FIG. 13 indicates the down-regulation of lncRNA-CTB89H12.4 after an AMI event resulted in up-regulation of hsa-miRNA-137 and activation of FTLH-17 mRNA with an increased translation and production of high levels of Nourin protein. There is none to a minimal gene expression of FTLH17 mRNA in normal non-stressed tissues. lncRNA-CTB89H12.4 is related to cardiomyocyte regeneration and angiogenesis and it is down-regulated after myocardial injury.
Figure 14:
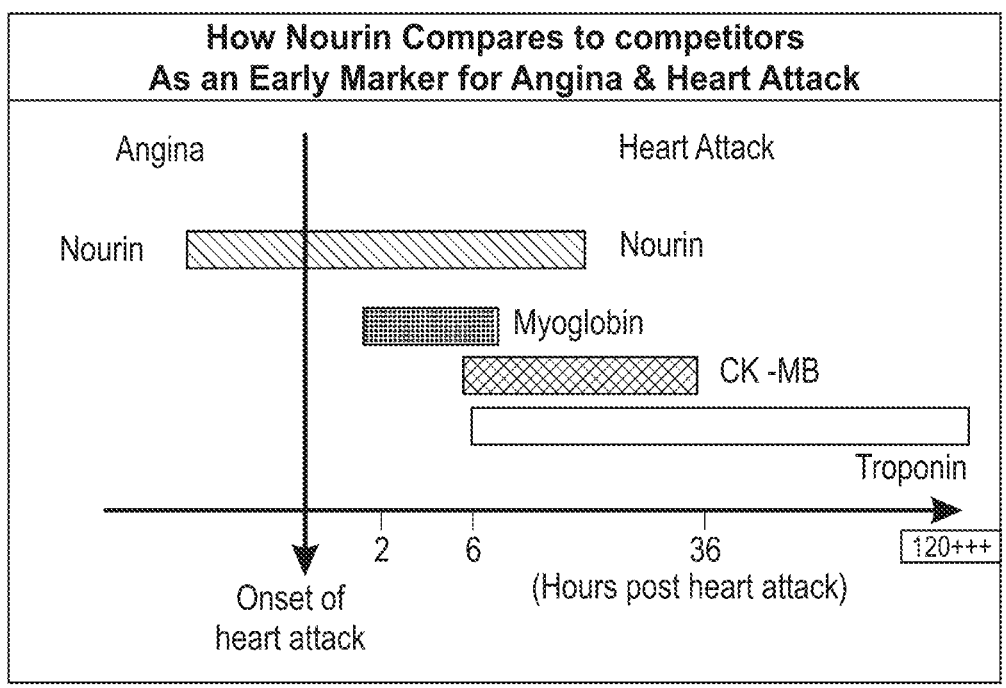
FIG. 14 indicates the timeframe under which various assays for UA and AMI are useful. Specifically, the figure indicates that the present Nourin assay can diagnose UA prior to a heart attack and it can be detected immediately after the initiation of AMI and up to at least 32 hours after an event. The Nourin protein was not tested beyond 32 hours after the onset of chest pain in AMI patients. The present Nourin assay is capable of diagnosing UA in patients, regardless of whether or not they ultimately suffer a heart attack. The myoglobin assay known in the art cannot detect UA and can detect AMI only between about 2 hours and 8 hours after AMI. The CK-MB assay known in the art likewise cannot detect UA, and is useful only between 6 hours and 36 hours after a heart attack. The Troponin assay is likewise limited to use only after 6 to 8 hours post-heart attack, although it can be detected up to 120 hours or more after an ischemic onset. Recent Troponin assays shortened the early detection time to 3 to 6 hours after the initiation of myocardial injury.

The present invention of the Nourin gene-based molecular biomarker panel composed of FTLH-17 mRNA, hsa-miRNA-137 and lncRNA-CTB89H12.4 further confirmed the use of the cardiac-derived Nourin protein as a biomarker of AMI patients. The down-regulation of lncRNA-CTB89H12.4 after an AMI event resulted in up-regulation of hsa-miRNA-137 and activation of FTLH-17 mRNA with an increased translation and production of high levels of the cardiac-derived Nourin protein (FIG. 13). There is a minimal gene expression of FTLH17 mRNA in normal non-stressed tissues. The Nourin RNA panel can be used individually or in combination with the protein-based biomarker Nourin for better and faster diagnosis of AMI patients presenting with chest pain to hospital ED and outpatient clinics. The Nourin molecular and protein-based assays are significantly earlier than current myoglobin, CK-MB and Troponin assays in detecting UA and AMI in patients presenting to the ED with chest pain (FIG. 14). Earlier identification of heart patients allows for early intervention to avoid permanent damage and heart attack that can lead to heart failure and death. In general, about 50% of heart attack patients suffer heart failure.

Although the currently identified circulating miRNA-208a, miRNA-133 and miRNA-1 peak in the blood at 3 hours after AMI, they are still markers of necrosis similar to Troponin. Nourin, on the other hand, is much earlier biomarker released by 'viable' ischemic tissue and, thus, provides fast diagnosis for crucial therapy (FIG. 14). Additionally, the low level of Nourin in blood samples collected from healthy individuals, makes Nourin an attractive diagnostic marker with little or no effect from normal non-stressed tissues. Furthermore, the Nourin RNA network will diagnose AMI with anterior STEMI, inferior STEMI as well as Non-STEMI (NSTEMI). Finally, Nourin panel of RNAs may be used to complement the protein-based Nourin and Troponin biomarkers as well as other classical risk factors for AMI diagnosis and prognosis. However, compared to protein-based biomarkers, RNA biomarkers have more sensitivity and specificity as it can be tissue and disease specific.

The Nourin assay using for example and not limited to Nourin including the Nourin panel of RNAs (qPCR, Nanogold, Multiplex, microfluidics and sensor ship) or Nourin epitope N-f-MII (leukocyte Chemotaxis, ELISA, sensor ship and MALDI-TOF [Matrix Assisted Laser Description Ionization-Time of Flight]) is expected to be used clinically in combination with Troponin for some better sensitive and specific diagnostic tests for acute coronary syndromes. The Nourin assays can identify unstable angina patients and complement and enhance the usefulness of Troponin tests to rule in or out unstable angina and AMI. If the Nourin assay does not detect elevated levels of Nourin RNA network and/or Nourin peptide, then ACS patients can be ruled out and the patients can be released from the hospital ED or a workup can begin to elucidate the true cause of the patients' chest pain syndromes. On the other hand, if the Nourin assay detect elevated levels of Nourin RNA network and/or Nourin peptide, the ACS patients can receive therapies in an earlier timeframe than is presently possible with current Troponin and thus eliminating the required long wait of 3 to 6 hours. Early identification of heart patients allows for early intervention to avoid permanent damage that can lead to ischemic heart failure and death. Specifically, early diagnosis of ischemic heart patients will allow for crucial intervention to avoid permanent damage and, thus, abort infarction, save heart muscles, reduce myocardial injury and the progression of patients to heart failure. In general, 50% of heart attack patients will suffer heart failure. The Nourin protein and its multiple genes that are functionally linked to each other and to AMI functional networks, increase the chance of a higher diagnostic success than the simpler conventional single-marker approach for Troponin. The Nourin assays will also be used to identify patients at risk for coronary artery disease (CDA) since circulating miRNAs were found to have a distinct pattern in cardiovascular disease including: CAD, AMI, hypertension, heart failure (HF) and viral myocarditis (VM). Thus, Nourin can be used not only for early diagnosis and monitoring of ACS patients presented to hospital ED and outpatient clinics with chest pain, but also as a risk predictive biomarker to (1) screen high-risk patients (diabetes, high blood pressure, obesity, aging, smokers, high cholesterol, stress, etc.) for the identification of CAD and allow for crucial intervention to avoid permanent damage, abort infarction, save heart muscles and reduce myocardial injury; (2) screen CAD patients for risk assessment to predict which patients are at risk for developing AMI; (3) predict drug therapy response on heart tissue in clinical trials; (4) monitor the heart health after therapy and disease progression; (5) differentiate cardiac from non-cardiac experiencing chest pain; (6) determine the risk level of heart patients experiencing chest pain; (7) provide risk stratification of AMI patients; and (8) diagnose heart failure patients after AMI and determine their risk assessment and prognosis.

It will be apparent to those skilled in the art that various modifications and variations can be made in the practice of the present invention without departing from the scope or spirit of the invention. Other embodiments of the invention will be apparent to those skilled in the art from considering of the specification and practice of the invention. It is intended that the specification and examples be considered as exemplary only, with a true scope and spirit of the invention being indicated by the following claims.

The invention claimed is:

1. A method for the diagnosis and differentiation of acute myocardial infarction (AMI) patients by Nourin protein and its novel autophagy-related Nourin gene-based RNA molecular network, comprising the steps of:
   a) identifying a novel autophagy-related Nourin gene-based RNA network;
   b) retrieving from the Nourin gene-based RNA network of step (a), Nourin gene-based RNA biomarkers, relevant to AMI and related to a Nourin peptide sequence, comprising:
      i) ferritin heavy polypeptide 17 (FTHL-17) gene for Nourin mRNA related to autophagy and cardiac ischemia,
      ii) homo sapiens micro RNA-137 (hsa-miRNA-137), an autophagy-related gene for cardiac ischemia as a regulatory gene on FTHL-17, and
      iii) long non-coding intergenic RNA (lnc-RNA-CTB89H12.4), an autophagy-related gene for cardiac ischemia and regulates hsa-miRNA-137;
   c) measuring and analyzing the Nourin gene-based RNA biomarkers from step (b) and Nourin protein levels in a sample, wherein the sample is fresh or frozen serum or plasma from a subject;
   d) using the analysis of the sample in step (c) for the diagnosis of an AMI patient at the presentation to hospital emergency department with symptoms of chest pain;
   e) differentiating the subject from whom the sample is obtained in step (c) into an AMI patient or a non-cardiac patient or a healthy control volunteer using the analysis of step (c) at the presentation to hospital emergency department with symptoms of chest pain,
   wherein, the Nourin peptide sequence in step (b) is formyl substituted-MIINHNLAAINSHR as set forth in SEQ ID NO:15 that is the N-terminus portion of the Nourin peptide sequence,
   wherein, the Nourin gene-based RNA biomarkers comprising, lncRNA-CTB89H12.4, hsa-miRNA-137, and FTHL-17 mRNA show differential expression as measured in step (c) in pathological cardiomyocytes as an autophagy-related RNA panel linked to each other and to cardiovascular ischemia to specifically identify ischemic cardiac events in AMI,
   wherein the Nourin protein levels as measured in step (c) show differential expression in pathological cardiomyocytes linked to the Nourin gene-based RNA biomarkers comprising, lncRNA-CTB89H12.4, hsa-miRNA-137, and FTHL-17 mRNA useful to differentiate the sample obtained from an AMI patient from the sample obtained from a non-cardiac patient or a healthy control volunteer at the presentation to hospital emergency department with symptoms of chest pain,
   wherein an up-regulation of the Nourin gene-based RNA biomarkers, hsa-miRNA-137, and FTHL-17 mRNA, with a down-regulation of the Nourin gene-based RNA biomarker, lncRNA-CTB89H12.4, and an up-regulation of Nourin protein levels provide the diagnosis of a sample as from an AMI patient, and
   wherein the differentiation is based on the absence of elevated levels of Nourin gene-based RNA molecular network consisting of the Nourin gene-based RNA biomarkers and Nourin protein level that rules out and differentiates AMI patients from non-cardiac patients and healthy control volunteers at the presentation to hospital emergency department with chest pains.

2. The method as claimed in claim 1, wherein the identification of the novel autophagy-related Nourin gene-based RNA network in step (a) is performed by the following steps consisting of:
   i) performing bioinformatic analysis using previous microarray and relating it to the Nourin peptide sequence, formyl substituted-MIINHNLAAINSHR as set forth in SEQ ID NO:16 that is the N-terminus portion of the Nourin peptide sequence to identify the RNAs in the Nourin gene-based RNA network which is used to retrieve Nourin gene-based RNAs as biomarkers; and
   ii) verifying said biomarkers by determining the expression level and pattern of Nourin gene-based RNAs in AMI patients' serum or plasma samples and comparing it to healthy control volunteers' samples using qPCR technique,
   and wherein the verifying of said step (ii) leads to retrieving of the Nourin gene-based RNA biomarkers of step (b) of claim 1.

3. The method as claimed in claim 1, wherein the identification of the novel autophagy-related Nourin gene-based RNA network to retrieve, measure, and analyze the retrieved the Nourin gene-based RNA biomarkers comprising, lncRNA-CTB89H12.4, hsa-miRNA-137, and FTHL-17 mRNA is performed alone or in combination with Nourin protein levels measured and analyzed in step (c) using an antibody to the Nourin polypeptide comprising the epitope sequence f-MII in the sample of step (c) of claim 1 under conditions where the antibody can specifically bind to said epitope and detect:
  i) binding of the antibody to the Nourin polypeptide comprising the epitope sequence f-MII;
  ii) binding that indicates that the sample is from a subject who experienced AMI;
  wherein the antibody to Nourin polypeptide comprising the epitope sequence f-MII is Nour001-A antibody.

4. The method as claimed in claim 1, wherein the method can early diagnose ischemic heart patients and allow for crucial intervention to avoid permanent damage and, thus, abort infarction, save heart muscles, reduce myocardial injury and the progression of patients to heart failure; complement and enhance the usefulness of Troponin tests to rule in or out unstable angina and AMI; provide risk stratification for AMI patients; identify at-risk patients for coronary artery disease (CAD) since miRNAs were found to have distinct patterns in cardiovascular disease including AMI, hypertension, heart failure, and viral myocarditis; diagnose heart failure patients after AMI and determine their risk assessment and prognosis; diagnose subclinical or silent myocardial ischemia without infarction as well as low-grade myocardial ischemia without cell death; screen heart transplantation patients' blood samples for cardiac allograft inflammation, and thus reduce heart biopsies; screen CAD patients for risk assessment to predict which patients are at risk for developing AMI; predict drug therapy response on heart tissue in clinical trials; monitor heart health after therapy and disease progression; and differentiate cardiac from non-cardiac patients presenting with chest pain to outpatient clinics and hospital Emergency Departments and determine the risk level of heart patients.

* * * * *

SEQUENCE LISTING

<160> NUMBER OF SEQ ID NOS: 19

<210> SEQ ID NO 1
<211> LENGTH: 88
<212> TYPE: RNA
<213> ORGANISM: Homo sapiens

<400> SEQUENCE: 1
acaaugcuuu gcuagagcug guaaaaugga accaaaucgc cucuucaaug gauuuggucc    60
ccuucaacca gcuguagcua ugcauuga                                      88

<210> SEQ ID NO 2
<211> LENGTH: 22
<212> TYPE: RNA
<213> ORGANISM: Homo sapiens

<400> SEQUENCE: 2
agcugguaaa auggaaccaa au                                            22

<210> SEQ ID NO 3
<211> LENGTH: 22
<212> TYPE: RNA
<213> ORGANISM: Homarus gammarus

<400> SEQUENCE: 3 uuugguccccc uucaaccagc ug                                           22

<210> SEQ ID NO 4
<211> LENGTH: 102
<212> TYPE: RNA
<213> ORGANISM: Homo sapiens

<400> SEQUENCE: 4
gguccucuga cucucuucgg ugacggguau ucuuggugug auaauacgga uuacguuguu    60
auugcuuaag aauacgcgua gucgaggaga guaccagcgg ca                     102

<210> SEQ ID NO 5
<211> LENGTH: 23
<212> TYPE: RNA
<213> ORGANISM: Homo sapiens

<400> SEQUENCE: 5 acgguauuc uuggguggau aau                                            23

<210> SEQ ID NO 6
<211> LENGTH: 23
<212> TYPE: RNA
<213> ORGANISM: Homo sapiens

<400> SEQUENCE: 6
uuauugcuua agaauacgcg uag                                           23

<210> SEQ ID NO 7
<211> LENGTH: 71
<212> TYPE: RNA
<213> ORGANISM: Homo sapiens

<400> SEQUENCE: 7
ugacgggcga gcuuuuggcc cggguuauac cugaugcuca cguauaagac gagcaaaaag    60
cuuguugguc a                                                        71

```
<210> SEQ ID NO 8
<211> LENGTH: 22
<212> TYPE: RNA
<213> ORGANISM: Homo sapiens

<400> SEQUENCE: 8
gagcuuuugg cccggguuau ac                                              22

<210> SEQ ID NO 9
<211> LENGTH: 22
<212> TYPE: RNA
<213> ORGANISM: Homo sapiens

<400> SEQUENCE: 9
auaagacgag caaaaagcuu gu                                              22

<210> SEQ ID NO 10
<211> LENGTH: 71
<212> TYPE: RNA
<213> ORGANISM: Homo sapiens

<400> SEQUENCE: 10
ugggaaacau acuucuuuau augcccauau ggaccugcua agcuauggaa uguaaagaag      60
uauguaucuc a                                                          71

<210> SEQ ID NO 11
<211> LENGTH: 22
<212> TYPE: RNA
<213> ORGANISM: Homo sapiens

<400> SEQUENCE: 11
acauacuucu uuauaugccc au                                              22

<210> SEQ ID NO 12
<211> LENGTH: 22
<212> TYPE: RNA
<213> ORGANISM: Homo sapiens

<400> SEQUENCE: 12
uggaauguaa agaaguaugu au                                              22

<210> SEQ ID NO 13
<211> LENGTH: 21
<212> TYPE: RNA
<213> ORGANISM: Homo sapiens

<400> SEQUENCE: 13
uuaagacuug cagugauguu u                                               21

<210> SEQ ID NO 14
<211> LENGTH: 22
<212> TYPE: RNA
<213> ORGANISM: Homo sapiens

<400> SEQUENCE: 14
aacaucacag caagucugug cu                                              22

<210> SEQ ID NO 15
<211> LENGTH: 31
<212> TYPE: PRT
<213> ORGANISM: Homo sapiens

<400> SEQUENCE: 15
```

Met Ile Ile Asn His Asn Leu Ala Ala Ile Asn Ser His Arg Ser Pro
1               5                   10                  15

Gly Ala Asp Gly Asn Gly Gly Glu Ala Met Pro Gly Gly Gly Arg
            20                  25                  30

<210> SEQ ID NO 16
<211> LENGTH: 14
<212> TYPE: PRT
<213> ORGANISM: Homo sapiens

<400> SEQUENCE: 16

Met Ile Ile Asn His Asn Leu Ala Ala Ile Asn Ser His Arg
1               5                   10

<210> SEQ ID NO 17
<211> LENGTH: 11
<212> TYPE: PRT
<213> ORGANISM: Mus musculus

<400> SEQUENCE: 17

Met Ile Ile Asn His Asp Asp Glu Arg Lys Cys
1               5                   10

<210> SEQ ID NO 18
<211> LENGTH: 11
<212> TYPE: PRT
<213> ORGANISM: Mus musculus

<400> SEQUENCE: 18

Met Ile Ile Asn His Asp Asp Glu Arg Lys Cys
1               5                   10

<210> SEQ ID NO 19
<211> LENGTH: 8636
<212> TYPE: DNA
<213> ORGANISM: Homo sapiens

<400> SEQUENCE: 19
caaatgccat tgaaaccgct agtcttattt cctttctact tttctttggc actcttactg       60
cctgtaagga gtagaactgt tagggcacac tgttgctata cagtttaact cccatttca      120 tgttttgtct ttcttttccc atttctgggg cttacctcct gatacctgct tactttctgg      180
aagtagtggg caagtaagat ttggctcttg gtttctaatt tttaaatttc tgaatactgc      240
cctagtctga acttggcctt tatagattaa tctttgcttc acattttag tgttgtattt      300 aaactatttt ataatttaaa aatagattct aatctgaaga tacttttcaa gaaatattat      360
taactgatgt catcctcatc ccagcagctc atctgttagg aatgaagttg agatgcttct      420
attccatgtt tttgtatttg ggaaggattc aaagttgaag gtttattgtc gttgggtttt      480
tcagatggtg acatgtaaac tcaggatagc aaaccctaat gttcacacag tgctctgcct      540
ctgcatctca gttgggatag ttgctccttt tgagtgtttt aatcatcgta taactaatca      600
tagtgccaag aagttcataa tgtgttatgt agctaatgtc actgaaaaac agtcctacca      660
ttttaggtaa gaccaaacag agtctctaac ccaaggactt gttacacctg acaacctata      720
gtatatttgc ttttctcac aaaatgaaac caattttgcc gaaagctagc tgggataata      780
ggatcatcac aagttgcagt tctataact aaaattagat tgaaatctct tctgacctag      840
aacattttac ttcaggcatt cagcagattt cagaaagaat tacctttatt taagttagtt      900
tctttgttag tttactgtgt gtctcttatt caataaacaa gcagaatttg tgtcctgccc      960

```
tatccatgtc ttaaagatga gaagttggat ccactgagtt agtttcattg gggcggggga      1020
aagaactgta attaaacttg tttaatcctt attttgtatt gtagctattt tttgtaaaag      1080
caacttaaaa tcttttaaaa attttatagt gacattagag acaatggtca tacaaattat      1140
cacataaaca tggacttgaa aaattaggct tttcataaaa cacatcacat gtcattgact      1200 gcttttta ga aatacacttc caaggcagta catctgtatt gctactgaaa agtgccattt      1260
cacagaacac agacttcttt ttgctctttg acatcttgaa aacatctgtt tttctttttt      1320
aatacaaaac tttgtgctca agacaaatct tacatgaaac tctcataaac catgaaaatg      1380
tagctggcct tcgggcctta ggcatgaaat aagcatgagg aacatattcc cctaacttct      1440 accccagcc cagcaagtta tccttttaaga aatctcctag gaattctgga gtttgaaaac      1500
aattgctcta tgttattcct gcttccagtc tctaagtaac aagggcattt aaaagcatag      1560
tctcttaagg tccactatag tggttctta tttaaggaat aactcagctg ggtgcagtgg       1620
ctcacgcctg ttatcccagc actttgagag gctgaggcaa gcagatcact tgaggccagg      1680
agttcgagag tctggccaac atggtggaaa cccatctcta caaaaaatac aaaaattagc      1740
caggtgtggt ggcgtgcacc tatggtccca gctatttggg aggctgaggc aggagaattg      1800
cttgaacctg ggaggtggag gttgcagtga gccaagattg tgccgctgca ctccagcctg      1860
ggtgacagag tgagactctg tctcaaaaaa aaaaaaaaa ggaactcata cagctcaatg      1920
attcattgat cccaataata aatcgtttta ataatgatga aaacatccta ctggggtttt      1980
cttgttaaaa actttaggac aggcgcagtg gctcatgcct gttattccaa cacatttggg      2040
aggctgaggt gggagaattg cttgacccta ggagttctag acttgcctgg gccacatagt      2100
aagaccctgt cccagctccc tccaacatcg tcccaaccc cccccccccc aaaaaaaaaa      2160
agcgccaggc gcagtagtga gtgcctgtga tcccagctgt gttgggaggc tgaggtggga      2220
gtatcacctg agccctggag gttgaggctg caatgagagc tgtgatcatg ccactgcact      2280
ccagcctggg caacagatga gaccctgtgt cacaacaagg aattttttaga aggtgctttt      2340 tatattactc ttcacagagt taaatttttca gaggatttag tattattgaa ctaagtttca      2400
taagtgtatt ttaagcaagt aaatctctaa tgtaggaaaa tccccaaaat ggtagcattt      2460
actaatgttt tatatggtaa ttttgaaaa atatatctga tatttcttca gtaaaaatgg      2520
tgttgtttta ataacttaat aagaatgttt aaagattctt taagtctggc ttatctagct      2580
aatgtgggcc tattaaataa taggcagact tctgccttcc ttatattctt tagatctttt      2640
caaatactcc attccaatat ccatcaaaag acttctcttt atgccactta ttatctatac      2700 tagttttta a tgttcaatta ctacaagatt ataattactg ttttattca tgttcccaag      2760 aaaaatacat aagattcaca cccaacacac ttcgaaattt atttcactcc ctttgactat      2820
atgtgattat caaaaagta ttttcaaga tattaaaaat aagtaaagga aaatgaaata       2880 ttttaggac attcaaaatc taatgaagtt cagtgtttct ttaattgagg gcaggcagag      2940
gtgggggaga atttcagaag gtagtgaacc caaaggtgga ttcttggata attctactat      3000
tctgtactct catcatctta acccatctgt ttactaccct aaccatagtt actaagcaga      3060
gttttatcat aataatatag acagctctca aagtattgac attcagaggg gattacaaat      3120 attattttc tatcatattg acctaccatg tccacagtct tccttgaatt accttccagt      3180
tttactgggc tgcatctacc gtttatgtct agtttgactt tttctgagtt caccaattgc      3240
tgctaggaat gtgctggtca ctcagcagca cacccacatc acaggggaag attttgaaat      3300
acctggacag tctgaacaca ctgctctgaa tacactcaat tctaagaagt accagggaac      3360
```

```
cgcatcttct tgctgaaatc ttgaattttt gtcagctttt tttttactg tggacagtaa      3420 agctggaaag atctaaataa cccaacagga aatgcggatg aaagtgcaag agttggtttg      3480
tggtcatctg gagtccatgt ctccaagact gctggacctt caaattctgc aacttgttag      3540
atcatctgga tgatagcaca actgttagaa gacctagaag aatacagcgt tgctatgact      3600
cagtggtgtt gaatgcagac catctaccag ctggggaaag aatcaattat aaacaggaat      3660
aaagggattc attcctcatt ttaactgatg ttacagtgaa gatgggttct tgaactcttg      3720
gaagcctgga tgagccacct aatctgcaag ataaaaacca agaccaatg cgtattgggg       3780 aaaagaatgc ttagtactgc aagactgttg aatacctgtt gaatattcct attgaggttt      3840
tttcctaaac atacttcagt aacatcttag acaattcac tggagaaatg ttgatccctg        3900 gctgaatgt cataccattg acccatttga agagttaaag ctggatttga ctgctctatt       3960
ctaccaggaa tattgttagg gtagcctttt accagtttct aaacaattgt aatcatttat      4020
tgactcagca attcctcaga taacaggtca aagatgtac agatacattc tgaagttttc       4080
ttgctattaa aggcacaaga gtttccttgt attttgactg acaatgtagc atgtttccat      4140
tttagtttgt tagtgatggt ggttttccct ttgaaagcca tttggtatat tcaccataac      4200
aattagttta atatgattac ataagaaaac tatgataaaa cccagcaatt ttagtagttg      4260
tgaaaatacg tttttaaat catgtttaag aagaattgca agacttgaaa ccaaatcctg       4320
atgggggaat tctgtttaat cctgtttaat ctgtttaatt tctgtttaat ccttagtttc     4380
ttaacctgca tagcttatcc tgtattgtac ttttttttctt ttttaaactc ccaaacaaga    4440
agcttgaaac ttttcctgta ttttaaaatt gaaatttggt cacagggtat agtcagattt     4500
ttattaaggt ttggtttgac aacctttaaa agaaaggttt acctcgctaa tacttcttaa     4560
taacatgcat caaatgatat tccctatggt gaagtatatt ctcaaagtta tgttatcttt    4620
catttttggc atttggtgct tatggactta gtacccaggc aacaaagatc tattatgcac     4680
ctactctctt gtatgttcgc tattatttcc caaaaaaaaa aagggggcata tatgcataag    4740 aaataaatat tagaattatt ttgtttctcc cacaaagccc atgggagatg gcccaacaaa    4800
tgtttaaaaa gtaaagaaag ctgggcacgg tggctcccac ctgtaaccccc cacactttgg    4860 gaggccatgg cgggtggatc acgaggtcag gagtttgaga ccagcctggc caacacagtg     4920
aaactgtgtc tctactataa atacaaaaat tagccaggca tggtggcagg cacctatagt     4980
cccagctact caggaggctg aggcaggaga atcgcttgaa cccaggaggc agaggttgcg     5040
gtgagccaag atcatgccac tgcccctccag cctgggtgac agagcgagac tgtctccaaa   5100
aaaaaagaaa aagaactaa aagaaaagga gcagtttatg attgaagaaa acatgacctg      5160
ggctgaagaa gtgaggattg attggagtgg gctagaatga gctatagttt ctagctcatt    5220
tgtaaggagg tagacaaagg agcattggtg cctcagagtg ggtgtctggt gagaggaaaa    5280
acggtgctta agagatttc aggctattgc tgtgggacag gcatattttc tcccttttgcc     5340 tttagctgta gataaagtgt ggttatgacc tgaggcttct tgtattcaaa cttggcctag    5400
ggcctatgta gaggccctag ggtctacttg tggtggagga gggaagtatt tgtagaatgt    5460
gtaggcttga gaagtaaata aagccaaaaa agcatcactt gcttacattt ttaaatgagt    5520
cacaaaacaa tctttctaat gcggccggta agaagttttt aaaggtctaa ggtttctcta    5580
cagaaattac atgcttctca ggtctttgtt tagtaaaata atacagataa ttatgctttg    5640
aatgcattta ttattaaagc taaccgttttt aatttgtgtc agaataatt tgtgcctatg    5700
```

```
gtaggattaa aattgtattc tttagttaaa gcaaagcaat ctgttttca ttgatttgat      5760 aaatatgtga atgcctaata tgttctgcat atgtaaaaat gcagaaacat gctcatttga      5820
attactaata attattttag tatgctgaga ggctttgaat tcactgtacc actccttcct      5880
agagtcattc aaaacagaaa aaattagttt taagtataga ttcatgtttt tctgttttaa      5940
aaagttgagc taatacttt cacaagagac gaaataacat gagccactat aattattggc      6000
tcagttccac ccaattttcca tatttttgggt gtaatttaaa attttttgact tggaattta      6060 acttttttt tgttttgatt ttttaccagg tttctaagca tgaattgagg aacagaagaa      6120
gcagagcaga tgatcggagc agcatttgtt tctccccaaa tctagaaatt ttagttcata      6180
tgtacactag ccagtggttg tggacaacca tttacttggt gtaaagaact taatttcagt      6240
ataaactgac tctgggcagc attggtgatg ctgtatcctg agttgtagcc tctgtaattg      6300
tgaatattaa ctgagatagt gaaacatggt gtccggtttt ctattgcatt ttttcaagtg      6360
gaaaagttaa ctaaatggtt gacacacaaa aattggtgga gaaattgtgc atatgccaat      6420
tttttgttaa aaccttttgt tttgaactat actgctttga gatctcattt cagaagaacg      6480
gcatgaacag tcttcagcca cagttgtgat ggttgttaaa tgctcacaat tgtgcattct      6540
tagggttttt ccatccctgg ggtttgcaag ttgttcactt aaaacattct taaaatggtt      6600
ggcttcttgt ctgcaagcca gctgatatgg tagcaaccaa agattccagt gtttgagcat      6660
atgaaagact ctgcctgctt aattgtgcta gaaataacag catctaaagt gaagacttaa      6720
gaaaaactta gtgactacta gattatcctt aggactctgc attaactcta taatgttctt      6780
ggtattaaaa aaaagcata tttgtcacag aaatttagtt aacatcttac aactgaacat      6840
gtatgtatgt tgcttagata aatgtaatca ctgtaaacat ctatatgatc tgggattttg      6900 ttttatttt gaaatgggag ctttttttgtt tacaagttca ttaaaaacta aaactgttt      6960 ctgtaaggaa atgagatttt ttttaaacaa caaaaaatgc cttgctgact cactattaaa      7020
taaaaatctc cccaatttt tgatagacta cttcaagcca tttgttacat ggtattcctt      7080
tgcaagtcaa tttaggtttc gtgttataac ttttcctctt tttttaagaa aaatgaaaaa      7140
agtaattctt ttgtctgaag gggaaaggca ttctttcatt tttttctttt ttttttttt      7200 tttttatgac ttgcaggcac aatatctagt actgcaactg ccagaacttg gtattgtagc      7260
tgctgcccgc tgactagcag ctggactgat tttgaataaa aatgaaagca ttaaagggtt      7320
tccctacaaa acattttcct ttaaaatact tttgaaatgg ctataagcag ttgactttca      7380
cccttggaga gcatcacact gtgtgaggtt cagtgattgt tgaccctccc cagcccctcc      7440
tgcttcttta agttatctgt gtgcgtgcgc ttcctctcaa tcttctttgc acgctcattt      7500 cttttctct gacccatgag aaaggaaaac ttactgatga taattttaa atagtgtaat      7560 ttattcattt atagcatgtc aggataaatt aaaagaacat ttgtctggaa atgctgccgg      7620
gagcctattg tgtaaatgta ggtattttgt aaaataaccct tgaaattgta aattgacacg      7680
tgtttggtca gattgtgtca agtttaattt gttttgtttt cttttttctt tttttattt      7740 gaaaactact ttagcaataa ttaattccat gattatcaca ttctgccatt aagggatatt      7800
agtaccgtaa tactgaagaa attttattaa gtctgaactt ctggggtagg cagcttcttt      7860 gtttctttc tatccaccct gtcggttgga ggtatttgtt tcttgactaa taaacccttt      7920 gatacttta gccagaaatc agtctcataa agctatttt gagtatagtt tgtgtaaaat      7980
aaaaatgttt agctttggta ataacttcca agctgaactc cctctagcaa gatatttttc      8040
agtgctttta tttactatgc acttagacta tgcacttttt ctgaaatatt tttgtaacac      8100
```

| | | | | |
|---|---|---|---|---|
| tttttttgtat | ttttgccatt | tgaaaaggtt | gtggtgtagt | tggtctgtaa ttaagttgca 8160 |
| gatttaaaac | tgctgttagc | tttgtaaatc | aaaatatagg | tgttttttgt cctggtatat 8220 |
| cgtcattcca | tctgcagctg | gagctggaat | cccattgatc | ttctagctac cattcatttt 8280 |
| cttcactgtt | cacaaaagaa | gagtgtgaaa | ttcagtgaat | gctgttacta atcctgttac 8340 |
| gagatgaatc | tcatttcacc | aaaattaaat | tatgtttttc | cgctaaaatg atgatacaag 8400 |
| ttgaagacac | atcactctga | aattggaaga | cctcaccact | taaggctcca cagtggctta 8460 |
| ctcagctgaa | ctctaggtta | ctactcttta | ctttgttcac | ccattggggg gtgcagtttt 8520 |
| tttaaaatgt | tgggagatgg | ccattctaac | tactgttgaa | tgtctctgtt ttgggaaggt 8580 |
| ataacaagaa | ataaaaaaga | atatatatga | agggagagac | tggttatctc ctccca 8636 |